United States Patent
Dedhar et al.

(10) Patent No.: US 7,655,780 B2
(45) Date of Patent: Feb. 2, 2010

(54) INTEGRIN-LINKED KINASE AND ITS USES

(75) Inventors: Shoukat Dedhar, Richmond (CA); Gregory E. Hannigan, Toronto (CA)

(73) Assignee: Sunnybrook and Women's College and Health Science Centre, Ontario (CA)

( * ) Notice: Subject to any disclaimer, the term of this patent is extended or adjusted under 35 U.S.C. 154(b) by 0 days.

(21) Appl. No.: 11/731,643

(22) Filed: Mar. 29, 2007

(65) Prior Publication Data

US 2008/0039419 A1 Feb. 14, 2008

Related U.S. Application Data

(63) Continuation-in-part of application No. 09/925,548, filed on Aug. 8, 2001, now abandoned, which is a continuation-in-part of application No. 09/390,425, filed on Sep. 3, 1999, now Pat. No. 6,338,958, which is a continuation of application No. 09/035,706, filed on Mar. 5, 1998, now Pat. No. 6,001,622, which is a continuation-in-part of application No. 08/955,841, filed on Oct. 21, 1997, now Pat. No. 6,013,782, which is a continuation-in-part of application No. 08/752,345, filed on Nov. 19, 1996, now abandoned.

(60) Provisional application No. 60/009,074, filed on Dec. 21, 1995.

(51) Int. Cl.
C07H 21/02 (2006.01)
C07H 21/04 (2006.01)

(52) U.S. Cl. ............... 536/23.2; 536/23.1; 536/23.5; 536/24.1; 536/24.5

(58) Field of Classification Search ........... 536/23.1, 536/23.2, 23.5, 24.1, 24.5
See application file for complete search history.

(56) References Cited

U.S. PATENT DOCUMENTS 6,001,622 A 12/1999 Dedhar et al.

FOREIGN PATENT DOCUMENTS

| WO | WO 94/21781 | 9/1994 |
|---|---|---|
| WO | WO 96/00760 | 1/1996 |
| WO | WO 96/36642 | 11/1996 |
| WO | WO 97/23625 | 7/1997 |

OTHER PUBLICATIONS

Clark et al., 2003, EST Accession No. AY411993 (computer printout pp. 18-20).*
Li et al., 2004, EST Accession No. AL555417, (computer printout pp. 26-27).*
Hirling et al., 1992, Nucleic Acid Research, vol. 20, No. 1, p. 33-39.*
Dedhar, S., "Integrin mediated signal transduction in oncogenesis: an overview," (1995) *Cancer and Metasis Reviews*, 14:165-172.
Dedhar, S., et al., "Integrin cytoplasmic interactions and bidirectional transmembrane signaling," (1996) *Current Opinion Cell Biol.*, 8:559-657.
Gimond, et al., (1995) *Exp. Cell Res.*, 216:232-235.
Givskov, et al., (1990) Swiss Prot_38 Accession P18954.
Genbank Accession No. H70160.
Genbank Accession No. R91874.
Hannigan, et al., "Regulation of cell adhesion and anchorage dependent growth by a new beta I integrin linked protein kinase," (1996) *Nature* 379:91-96.
Hannigan, et al., "Overexpression of a novel integrin linked kinase (ILK) induces a transformed phenotype and cyclin D1 expression," (1995) *Molecular Biology of the Cell*, 6:2244.
Hannigan, et al., "Cloning of a novel protein kinase associated with beta I integrin cytoplasmic tails," (1995) $80^{th}$ *Annual Meeting of the American Association for Cancer Research*, P:361.
Kappel, C., et al., (1992) *Current Opinion in Biotechnology*, 3:548-553.
Lin, T., et al., "Integrin-mediated tyrosine phosphorylation and cytokine message induction in monocytic cells," (1995) *The Journal of Biological Chemistry*, 270(27):16189-16197.
Liao, L., et al., "Effect of α-protein kinase C, neutralizing antibodies and the pseudosubstrate peptide on phosphorylation, migration and growth of REF52 cells," (1993) *Cell Growth and Differentiation*, 4:309-316.
Dedhar, S., et al. (1997) Geneseq Accession No. AAT71716, computer printout, pp. 4-5.
Adams, et al. (1997) EST Accession No. AA295328, computer printout, p. 2.
Hillier, et al. (1997) EST Accession No. AA135079, computer printout, pp. 6-7.
Hillier, et al. (1995) Genbank Accession No. R14703, pp. 4-5.
Ozaki, et al. (1993) Genbank Accession No. D13973, pp. 12-13.

* cited by examiner

*Primary Examiner*—Shin-Lin Chen
(74) *Attorney, Agent, or Firm*—Bozicevic, Field & Francis LLP; Pamela J. Sherwood

(57) ABSTRACT

ILK genetic sequences and methods of use are provided. In some embodiments, a fragment or portion of an ILK polynucleotide is provided, where the polynucleotide has a sequence consisting of contiguous nucleotides within the provided ILK sequences, which may be within the provided ILK coding sequences. Such polynucleotides may be DNA, RNA, and the like, and may be double stranded or single stranded.

24 Claims, No Drawings

INTEGRIN-LINKED KINASE AND ITS USES

CROSS-REFERENCE TO RELATED APPLICATIONS

This application is a continuation-in-part of U.S. patent application Ser. No. 09/925,548, which is a continuation-in-part of U.S. patent application Ser. No. 09/390,425, filed Sep. 3, 1999 now issues as U.S. Pat. No. 6,338,958, which is a continuation of U.S. patent application Ser. No. 09/035,706, filed Mar. 5, 1998, now issued as U.S. Pat. No. 6,001,622, which is a continuation-in-part of U.S. patent application Ser. No. 08/955,841 filed Oct. 21, 1997, now issued as U.S. Pat. No. 6,013,782, which is a continuation-in-part of U.S. patent application Ser. No. 08/752,345, filed Nov. 19, 1996, now abandoned, which claims priority to provisional patent application No. 60/009,074, filed Dec. 21, 1995; each of which is herein specifically incorporated by reference.

INTRODUCTION

Background

Research on signal transduction over the years has clearly established the importance of direct, protein-protein interactions in the cytoplasm as a major mechanism underlying the specification of signaling pathways. These interactions can, in part, be those between a receptor and a cytoplasmic protein kinase, or between a protein kinase and its substrate molecule(s).

It is known that kinases can form complex signaling cascades, where the activation of one kinase causes it to activate or de-activate another kinase, and so forth through several iterations. One advantage to this type of pathway is that a single "second messenger" can affect a number of different processes, depending on the specific kinase expression pattern in a cell. A particularly interesting second messenger in this respect is phosphatidylinositol 3,4,5 triphosphate [PtdIns(3,4,5)$P_3$]. [PtdIns(3,4,5)$P_3$] acts on pathways that control cell proliferation, cell survival and metabolic changes—often through protein kinases. This lipid can be produced by PI3 kinases, a family of related proteins (Van haesebroeck et al. (1997) TIBS 22:267; Toker and Cantley (1997) Nature 387:673676). One downstream effector is protein kinase B (PKB/AKT) (Downward (1998) Science 279:673-674). PKB contains a pleckstrin homology (PH) domain, to which the [PtdIns(3,4,5)$P_3$] signaling molecule binds. In addition, PKB itself is phosphorylated when [PtdIns(3,4,5)$P_3$] is present, by two different protein kinases, one of which has been cloned (Stephens et al. (1998) Science 279:710-714; Alessi et al. (1997) Curr. Biol. 7:776). The molecular identity of the other kinase has not previously been established. The determination of this kinase, as well as its substrates and modulators, is of great interest for providing a point of intervention in this pathway.

If it were determined that a specific kinase regulates integrin function, products that regulate the activity of that kinase could be used for the treatment of cancer, leukemia, solid tumors, chronic inflammatory disease, restenosis, diabetes, neurological disorders, arthritis and osteoporosis, among other indications.

Relevant Literature

A review of integrin mediated signal transduction in oncogenesis may be found in Dedhar (1995) Cancer Metastasis Rev 14:165-172. Hannigan et al. (1995) 86th Annual Meeting of the American Institute for Cancer Research, provide a brief abstract directed to the cloning of a novel protein kinase associated with beta integrin cytoplasmic tails. Hannigan et al. (1995) Molecular Biology of the Cell suppl. 6, p. 2244, is an abstract directed to the effect of overexpression of a novel integrin linked kinase (ILK) in induction of a transformed phenotype and cyclin D1 expression. Rosales et al. (1995) Biochim Biophys Acta 1242:77-98 reviews signal transduction by cell adhesion receptors. Signaling by cell adhesion receptors may, involve aspects that impinge on previously known signaling pathways including the RTK/Ras pathway and serpentine receptor/G protein pathways. A possible signaling role for the Syk tyrosine kinase is described in Lin et al. (1995) J Biol Chem 270:16189-16197.

Miyamoto et al. (1995) Science 267:883-885 compare the roles of receptor occupancy and aggregation on integrin receptor mediation of cell adhesion, signal transduction, and cytoskeletal organization. An EST sequence is provided by EMBL sequence DNA library accession no. p H70160, the Wash. U.—Merck EST project.

The sequences of a number of kinases are known in the art, including human protein kinase B (Coffer and Woodgett (1991) Eur. J. Biochem. 201:475-481). PI3 kinases have been characterized, including phosphatidylinositol 3-kinase gamma polypeptide, (OMIM 601232); phosphatidylinositol 3-kinase alpha polypeptide (OMIM 171834); phosphatidylinositol 3-kinase regulatory subunit (OMIM 171833); mouse PI3 kinase (Genbank M60651); rat PI3 kinase (Genbank D78486, D64045). Glycogen synthase kinase 3 sequences can be accessed at Genbank; the human cDNA sequence has the accession number L40027.

SUMMARY OF THE INVENTION

Isolated nucleotide compositions and sequences are provided for integrin linked kinase (ILK) genes. In some embodiments, a fragment or portion of an ILK polynucleotide is provided, where the polynucleotide has a sequence consisting of contiguous nucleotides within the provided ILK sequence, which may be within the provided ILK coding sequence. Such polynucleotides may be DNA, RNA, and the like, and may be double stranded or single stranded.

The ILK nucleic acid compositions find use in identifying homologous or related genes; for production of the encoded kinase; in producing compositions that modulate the expression or function of its encoded protein; for gene therapy; mapping functional regions of the protein; and in studying associated physiological pathways, as anti-sense reagents, etc. In addition, modulation of the gene activity in vivo is used for prophylactic and therapeutic purposes, such as treatment of cancer, identification of cell type based on expression, and the like.

DESCRIPTION OF THE SPECIFIC EMBODIMENTS

Nucleic acid compositions encoding integrin linked kinase (ILK) are provided. The ILK gene product (herein p59ILK) is a serine threonine kinase having two functional domains, the catalytic domain, responsible for phosphotransferase activity (kinase domain), and a non-overlapping domain in the amino terminus, comprised of four contiguous ankyrin-like repeats. Modulation of ILK gene activity in vivo is used for prophylactic and therapeutic purposes.

For example, the down-regulation of ILK by administration of anti-sense oligonucleotides is useful as treatment of cancer, investigation of integrin signaling pathway function, identification of cell type based on expression, and the like. Products that modulate the expression and/or activity of ILK have a therapeutic effect in the treatment of cancer, leukemia, solid tumors, chronic or acute inflammatory disease, restenosis, diabetes, neurological disorders, arthritis and osteoporosis, among other indications.

Characterization of ILK

The human gene sequence of ILK is provided as SEQ ID NO:1 or SEQ ID NO:100, the encoded polypeptide product as SEQ ID NO:2 or SEQ ID NO:101. The ILK protein is encoded by a 1.8 kilobase pair messenger RNA (1.8 kb mRNA). The coding sequence extends in SEQ ID NO:1 from residue 157 to residue 1515; and in SEQ ID NO:100 from residue 157 to 1512.

The sequence of this mRNA was used to deduce the primary amino acid sequence of the protein, which has a predicted molecular weight of 50 kiloDaltons (kDa). The recombinant protein migrates on analytical polyacrylamide electrophoresis gels with an apparent molecular weight of 59 kDa, in rough agreement with the predicted size. The ILK chromosomal locus is mapped to region 11p15.

ILK has novel structural and functional features. The molecular architecture is unusual, in that a protein kinase and an ankyrin repeat domain are contained within the same protein. The kinase domain has a high degree of similarity to other kinase sequences in existing databases, and can be divided into typical subdomains (I through XI) based on this conserved structure. However one amino acid in subdomain VIb of all other protein kinase domains is not present in ILK. Despite this unique structural feature, ILK clearly acts as a protein kinase, and thus represents a prototype member of a new subfamily of protein kinase molecules.

The function of ankyrin repeats in ILK is to mediate protein-protein interactions. The ILK ankyrin repeat domain is not required for the binding of $P59_{ILK}$ to integrin, and it is predicted to mediate the interaction of $P59_{ILK}$ with other cellular protein(s). Thus, $P59_{ILK}$ bridges integrin in the plasma membrane with intracellular proteins active regulating the cell's response to ECM signals. These proteins are likely to be located in the cytoplasm, or as part of the cell's structural framework (cytoskeleton).

The amino acid sequence of ILK contains a sequence motif found in pleckstrin homology (PH) domains (Klarulund et al. (1997) Science 275:1927-1930). This motif has been shown to be involved in the binding of phosphatidylinositol phosphates (Lemmon et al. (1996) Cell 85:621-624). Amino acids critical to the binding of such lipids to the PH domain are completely conserved in ILK. The phosphatidylinositol 3,4, 5, triphosphate binding sites are the lysines at positions 162 and 209 (SEQ ID NO:2). The PH motifs are comprised of residues 158-165 and 208-212 (SEQ ID NO:2). There is a high degree of sequence identity within this motif between ILK and other PH-domain containing proteins such as cytohesin-1 (a β2 integrin cytoplasmic domain interacting protein) and GRP-1. It was determined that ILK activity is influenced by the presence of phosphatidylinositol3,4,5, triphosphate, and interacts with other kinase proteins in this pathway.

ILK activity can be stimulated by phosphatidylinositol 3,4,5 trisphosphate in vitro. Both insulin and fibronectin can rapidly stimulate ILK activity in a phosphoinositide-3OH kinase (PI(3)K)-dependent manner. In addition, constitutively active PI(3)K activates ILK. The activated ILK can then inhibit the activity of glycogen synthase kinase-3 (GSK-3), contributing to ILK induced nuclear translocation of β-catenin. ILK can also phosphorylate protein kinase B (PKB/AKT) on serine-473, resulting in its activation, demonstrating that ILK is involved in agonist stimulated PI(3)K-dependent PKB/AKT activation.

In untransformed intestinal epithelial cells, the kinase activity of ILK is inhibited upon cell-extracellular matrix interactions, and overexpression of constitutively active ILK results in anchorage-independent growth and tumorigenicity in nude mice. A consequence of elevation of ILK levels is a disruption of cell-cell interactions and manifestation of fibroblastic cell morphology and phenotypic properties, which include formation of a fibronectin matrix and invasion of collagen gels.

Overexpression of ILK results in a downregulation of E-cadherin expression, formation of a complex between β-catenin and the HMG transcription factor, LEF-1, translocation of β-catenin to the nucleus, and transcriptional activation by this LEF-1/β-catenin complex. LEF-1 protein expression is rapidly modulated by cell detachment from the extracellular matrix, and LEF-1 protein levels are constitutively upregulated upon ILK overexpression. These effects are specific for ILK.

Overexpression of ILK stimulates fibronectin matrix assembly in epithelial cells. The integrin-linked kinase activity is involved in transducing signals leading to the up-regulation of fibronectin matrix assembly, as overexpression of a kinase-inactive ILK mutant fails to enhance the matrix assembly. The increase in fibronectin matrix assembly is accompanied by a substantial reduction in cellular E-cadherin. The increased fibronectin matrix assembly is associated with an increased potential for tumor growth in vitro and in vivo.

ILK Genetic Sequences

Homologs of ILK are identified by any of a number of methods. A fragment of the provided cDNA may be used as a hybridization probe against a cDNA library from the target organism of interest, where low stringency conditions are used. The probe may be a large fragment, or one or more short degenerate primers. Nucleic acids having sequence similarity are detected by hybridization under low stringency conditions, for example, at 50° C. and 10×SSC (0.9 M saline/0.09 M sodium citrate) and remain bound when subjected to washing at 55° C. in 1×SSC. Sequence identity may be determined by hybridization under stringent conditions, for example, at 50° C. or higher and 0.1×SSC (9 mM saline/0.9 mM sodium citrate). Nucleic acids that are substantially identical to the provided ILK sequences, e.g. allelic variants, genetically altered versions of the gene, etc., bind to the provided ILK sequences under stringent hybridization conditions. By using probes, particularly labeled probes of DNA sequences, one can isolate homologous or related genes. The source of homologous genes may be any species, e.g. primate species, particularly human; rodents, such as rats and mice, canines, felines, bovines, ovines, equines, yeast, nematodes, etc.

Between mammalian species, e.g. human and mouse, homologs have substantial sequence similarity, i.e. at least 75% sequence identity between nucleotide sequences. Sequence similarity is calculated based on a reference sequence, which may be a subset of a larger sequence, such as a conserved motif, coding region, flanking region, etc. A reference sequence will usually be at least about 18 nt long, more usually at least about 30 nt long, and may extend to the complete sequence that is being compared. Algorithms for sequence analysis are known in the art, such as BLAST, described in Altschul et al. (1990) J Mol Biol 215:403-10. The sequences provided herein are essential for recognizing ILK related and homologous proteins in database searches.

Nucleic acids encoding ILK may be cDNA or genomic DNA or a fragment thereof. The term ILK gene shall be intended to mean the open reading frame, encoding specific ILK polypeptides, introns, as well as adjacent 5 and 3 non-coding nucleotide sequences involved in the regulation of expression, up to about 20 kb beyond the coding region, but possibly further in either direction. The gene may be introduced into an appropriate vector for extrachromosomal maintenance or for integration into a host genome. The term cDNA as used herein is intended to include all nucleic acids that share the arrangement of sequence elements found in native mature mRNA species, where sequence elements are exons and 3 and 5 non-coding regions. Normally mRNA species have contiguous exons, with the intervening introns, when present, removed by nuclear RNA splicing, to create a continuous open reading frame encoding a ILK protein.

A genomic sequence of interest comprises the nucleic acid present between the initiation codon and the stop codon, as defined in the listed sequences, including all of the introns that are normally present in a native chromosome. It may further include the 3 and 5 untranslated regions found in the mature mRNA. It may further include specific transcriptional and translational regulatory sequences, such as promoters, enhancers, etc., including about 1 kb, but possibly more, of flanking genomic DNA at either the 5 or 3 end of the transcribed region. The genomic DNA may be isolated as a fragment of 100 kbp or smaller; and substantially free of flanking chromosomal sequence. The genomic DNA flanking the coding region, either 3' or 5', or internal regulatory sequences as sometimes found in introns, contains sequences required for proper tissue and stage specific expression. Sequences of interest also include sequences that cross intron/exon borders.

Double or single stranded fragments may be obtained of the polynucleotide sequence by chemically synthesizing oligonucleotides in accordance with conventional methods, by restriction enzyme digestion, by PCR amplification, etc. For the most part, polynucleotide fragments will be of at least 12 contiguous nt, usually at least 16 contiguous nt, 18 contiguous nt or 20 contiguous nt, and may be at least about 50 contiguous nt. Such small polynucleotide fragments are useful as primers for PCR, hybridization screening probes, as antisense reagents, etc. Fragments may be single or double stranded, and may run in the sense or anti-sense direction. Larger DNA fragments, i.e. greater than 100 contiguous nt are useful for production of the encoded polypeptide. Regions of the provided sequence that are of interest as fragments include the coding region of SEQ ID NO:1 or SEQ ID NO:100; the untranslated 5' or 3' sequences present in ILK mRNA; in particular the 5' end of the gene, i.e. a portion of the sequence set forth in SEQ ID NO:1 or SEQ ID NO:100, nucleotides 1 to 1100, for example the 5' untranslated region and the coding region. In some embodiments, fragments are other than the sequence set forth in Genbank accession number R14703, which include SEQ ID NO:1 or SEQ ID NO:100, residues 275-703.

The ILK genes are isolated and obtained in substantial purity, generally as other than an intact chromosome. Usually, the DNA will be obtained substantially free of other nucleic acid sequences that do not include a ILK sequence or fragment thereof generally being at least about 50%, usually at least about 90% pure and are typically recombinant, i.e. flanked by one or more nucleotides with which it is not normally associated on a naturally occurring chromosome.

Anti-Sense Oligonucleotides

As used herein, the term anti-sense oligonucleotides (ODN) is used to refer to an oligonucleotide molecule or analog thereof that is complementary to at least a portion of the ILK coding sequence, or the untranslated 5' or 3' sequences present in ILK mRNA, e.g. an oligonucleotide complementary to the sequence provided in SEQ ID NO:1. Specific examples of oligonucleotide sequences of interest for this purpose may be found in the Examples, SEQ ID NO:13-109.

Antisense molecules are used to down-regulate expression of ILK in cells. The antisense reagent may comprise naturally occurring nucleic acids, e.g. RNA or DNA; synthetic ODN having chemical modifications from native nucleic acids; or nucleic acid constructs that express such anti-sense molecules as RNA. Antisense molecules inhibit gene expression through various mechanisms, e.g. by reducing the amount of mRNA available for translation, through activation of RNAse H, or steric hindrance. One or a combination of antisense molecules may be administered, where a combination may comprise multiple different sequences.

Antisense molecules may be produced by expression of all or a part of the target gene sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 500, usually not more than about 50, more usually not more than about 35 nucleotides in length, where the length is governed by efficiency of inhibition, specificity, including absence of cross-reactivity, and the like.

Antisense oligonucleotides can be chemically synthesized by methods known in the art (see Wagner et al. (1993) supra. and Milligan et al., supra.) In one embodiment, the oligonucleotides are chemically modified from the native phosphodiester structure, in order to increase their intracellular stability and binding affinity. A number of such modifications have been described in the literature, which alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O-5'-S-phosphorothioate, 3'-S'-5O-phosphorothioate, 3'-CH$_2$-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The α-anomer of deoxyribose may be used, where the base is inverted with respect to the natural β-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5'-methyl-2'-deoxycytidine and 5'-bromo-2'-deoxycytidine for deoxycytidine. 5'-propynyl-2'-deoxyuridine and 5'-propynyl-2'-deoxycytidine have been shown to increase affinity and biological activity when substituted for deoxythymidine and deoxycytidine, respectively.

Antisense Modulation of ILK Expression

From a therapeutic point of view, inhibiting ILK activity has a therapeutic effect on a number of proliferative disorders, including inflammation, restenosis, and cancer. Inhibition is achieved in a number of ways. Antisense ILK sequences may be administered to inhibit expression. Where the antisense reagent is a transcribed gene product, an expression vector is used to transcribe the reverse strand (with reference to the normal mRNA coding sequence), where the transcription product may be all or part of the ILK sequence, e.g. as set forth in SEQ ID NO:1. Alternatively, where the antisense reagent is an oligonucleotide, the sequences will be administered in a suitable formulation, as described in detail below.

Expression vectors generally have convenient restriction sites located near the promoter sequence to provide for the insertion of nucleic acid sequences. Transcription cassettes may be prepared comprising a transcription initiation region, the target gene or fragment thereof, and a transcriptional termination region. The transcription cassettes may be introduced into a variety of vectors, e.g. plasmid; retrovirus, e.g. lentivirus; adenovirus; and the like, where the vectors are able to transiently or stably be maintained in the cells, usually for a period of at least about one day, more usually for a period of at least about several days to several weeks.

The gene or ILK protein may be introduced into tissues or host cells by any number of routes, including viral infection, microinjection, or fusion of vesicles. Jet injection may also be used for intramuscular administration, as described by Furth et al. (1992) Anal Biochem 205:365-368. The DNA may be coated onto gold microparticles, and delivered intradermally by a particle bombardment device, or "gene gun" as described in the literature (see, for example, Tang et al. (1992) Nature 356:152-154), where gold microprojectiles are coated with the ILK or DNA, then bombarded into skin cells.

The antisense compounds are administered to a subject having undesirable levels of ILK, for example associated with hyperproliferative disorders, e.g. to inhibit tumor growth, to inhibit angiogenesis, to decrease inflammation associated with a lymphoproliferative disorder, to inhibit graft rejection, or neurological damage due to tissue repair, etc. The present compounds are useful for prophylactic or therapeutic purposes. As used herein, the term "treating" is used to refer to both prevention of disease, and treatment of pre-existing conditions. The prevention of proliferation is accomplished by administration of the subject compounds prior to development of overt disease, e.g. to prevent the regrowth of tumors, prevent metastatic growth, diminish restenosis associated with cardiovascular surgery, etc. Alternatively the compounds are used to treat ongoing disease, by stabilizing or improving the clinical symptoms of the patient.

The host, or patient, may be from any mammalian species, e.g. primate sp., particularly humans; rodents, including mice, rats and hamsters; rabbits; equines, bovines, canines, felines; etc. Animal models are of interest for experimental investigations, providing a model for treatment of human disease.

The susceptibility of a particular cell to treatment with the subject compounds may be determined by in vitro testing. Typically a culture of the cell is combined with a subject compound at varying concentrations for a period of time sufficient to allow the active agents to induce cell death or inhibit migration, usually between about one h and one week. For in vitro testing, cultured cells from a biopsy sample may be used. The viable cells left after treatment are then counted.

The dose will vary depending on the specific compound utilized, specific disorder, patient status, etc. Typically a therapeutic dose will be sufficient to substantially decrease the undesirable cell population in the targeted tissue, while maintaining patient viability. Treatment will generally be continued until there is a substantial reduction, e.g. at least about 50%, decrease in the cell burden, and may be continued until there are essentially none of the undesirable cells detected in the body.

The compounds also find use in the specific inhibition of signaling pathway mediated by ILK. Protein kinases such as ILK are involved in signaling pathways for such important cellular activities as responses to extracellular signals and cell cycle checkpoints. Inhibition of specific protein kinases provides a means of intervening in these signaling pathways, for example to block the effect of an extracellular signal, etc. Defects in the activity of protein kinases are associated with a variety of pathological or clinical conditions, where there is a defect in signaling mediated by protein kinases.

It is also known that many cell types undergo apoptosis if the appropriate contacts with extracellular matrix proteins are not maintained (anoikis). The induction of apoptosis by the subject compounds in such cells predicts an association with the ILK signaling pathway.

There are many disorders associated with a dysregulation of cellular proliferation. The conditions of interest include, but are not limited to, the following conditions.

The subject methods are applied to the treatment of a variety of conditions where there is proliferation and/or migration of smooth muscle cells, and/or inflammatory cells into the intimal layer of a vessel, resulting in restricted blood flow through that vessel, i.e. neointimal occlusive lesions. Occlusive vascular conditions of interest include atherosclerosis, graft coronary vascular disease after transplantation, vein graft stenosis, peri-anastomatic prosthetic graft stenosis, restenosis after angioplasty or stent placement, and the like.

Diseases where there is hyperproliferation and tissue remodelling or repair of reproductive tissue, e.g. uterine, testicular and ovarian carcinomas, endometriosis, squamous and glandular epithelial carcinomas of the cervix, etc. are reduced in cell number by administration of the subject compounds.

Tumor cells are characterized by uncontrolled growth, invasion to surrounding tissues, and metastatic spread to distant sites. Growth and expansion requires an ability not only to proliferate, but also to down-modulate cell death (apoptosis) and activate angiogenesis to produce a tumor neovasculature. Angiogenesis may be inhibited by affecting the cellular ability to interact with the extracellular environment and to migrate, which is an integrin-specific function, or by regulating apoptosis of the endothelial cells. Integrins function in cell-to-cell and cell-to-extracellular matrix (ECM) adhesive interactions and transduce signals from the ECM to the cell interior and vice versa. Since these properties implicate integrin involvement in cell migration, invasion, intra- and extravasation, and platelet interaction, a role for integrins in tumor growth and metastasis is obvious. The involvement of integrins with leukocyte homing is also known, and such processes can be modulated by administration of ILK anti-sense reagents.

Tumors of interest for treatment include carcinomas, e.g. colon, duodenal, prostate, breast, melanoma, ductal, hepatic, pancreatic, renal, endometrial, stomach, dysplastic oral mucosa, polyposis, invasive oral cancer, non-small cell lung carcinoma, transitional and squamous cell urinary carcinoma etc.; neurological malignancies, e.g. neuroblastoma, gliomas, etc.; hematological malignancies, e.g. childhood acute leukaemia, non-Hodgkin's lymphomas, chronic lymphocytic leukaemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like.

Other hyperproliferative diseases of interest relate to epidermal hyperproliferation, tissue remodelling and repair. For example, the chronic skin inflammation of psoriasis is associated with hyperplastic epidermal keratinocytes as well as infiltrating mononuclear cells, including CD4+ memory T cells, neutrophils and macrophages.

The proliferation of immune cells is associated with a number of autoimmune and lymphoproliferative disorders. Diseases of interest include multiple sclerosis, rheumatoid arthritis and insulin dependent diabetes mellitus. Evidence suggests that abnormalities in apoptosis play a part in the pathogenesis of systemic lupus erythematosus (SLE). Other lymphoproliferative conditions the inherited disorder of lymphocyte apoptosis, which is an autoimmune lymphoproliferative syndrome, as well as a number of leukemias and lymphomas.

Formulations

The antisense reagents of this invention can be incorporated into a variety of pharmaceutical formulations for therapeutic administration. Particularly, such reagents are formulated for administration to patients for the treatment of ILK dysfunction, where the ILK activity is undesirably high, e.g. to reduce the level of ILK in cancer cells. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Compositions and formulations for oral administration include powders or granules, suspensions or solutions in water or non-aqueous media, capsules, sachets or tablets. Thickeners, flavoring agents, diluents, emulsifiers, dispersing aids or binders may be desirable. Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be prepared and formulated as emulsions. Emulsions are typically heterogenous systems of one liquid dispersed in another in the form of droplets usually exceeding 0.1 .mu.m in diameter. Emulsions may contain additional components in addition to the dispersed phases and the active drug which may be present as a solution in either the aqueous phase, oily phase or itself as a separate phase. Pharmaceutical excipients such as emulsifiers, stabilizers, dyes, and anti-oxidants may also be present in emulsions as needed. In one embodiment of the present invention, the compositions of oligonucleotides and nucleic acids are formulated as microemulsions. Typically microemulsions are systems that are prepared by first dispersing an oil in an aqueous surfactant solution and then adding a sufficient amount of a fourth component, generally an intermediate chain-length alcohol to form a transparent system. Microemulsions commonly are prepared via a combination of three to five components that include oil, water, surfactant, cosurfactant and electrolyte.

Other surfactant structures include monolayers, micelles, bilayers and vesicles. As used in the present invention, the term "liposome" means a vesicle composed of amphiphilic lipids arranged in a spherical bilayer or bilayers. Liposomes are unilamellar or multilamellar vesicles that have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo. Liposomes obtained from natural phospholipids are biocompatible and biodegradable; liposomes can incorporate a wide range of water and lipid soluble drugs; liposomes can protect encapsulated drugs in their internal compartments from metabolism and degradation. Because the liposomal membrane is structurally similar to biological membranes, when liposomes are applied to a tissue, the liposomes start to merge with the cellular membranes. As the merging of the liposome and cell progresses, the liposomal contents are emptied into the cell where the active agent may act. Liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Pharmaceutical carriers or excipients may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like. Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used. Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation. Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include, but are not limited to, anticancer drugs such as daunorubicin, dactinomycin, doxorubicin, bleomycin, mitomycin, nitrogen mustard, chlorambucil, melphalan, cyclophosphamide, 6-mercaptopurine, 6-thioguanine, cytarabine (CA), 5-fluorouracil (5-FU), floxuridine (5-FUdR), methotrexate (MTX), colchicine, vincristine, vinblastine, etoposide, teniposide, cisplatin and diethylstilbestrol (DES). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Other non-antisense chemotherapeutic agents are also within the scope of this invention. Two or more combined compounds may be used together or sequentially. In another related embodiment, compositions of the invention may contain one or more antisense compounds, particularly oligonucleotides, targeted to ILK. Two or more combined compounds may be used together or sequentially.

Experimental

The following examples are put forth so as to provide those of ordinary skill in the art with a complete disclosure and description of how to make and use the subject invention, and are not intended to limit the scope of what is regarded as the invention. Efforts have been made to ensure accuracy with respect to the numbers used (e.g. amounts, temperature, concentrations, etc.) but some experimental errors and deviations should be allowed for. Unless otherwise indicated, parts are parts by weight, molecular weight is average molecular weight, temperature is in degrees centigrade; and pressure is at or near atmospheric.

EXAMPLE 1

Isolation of ILK cDNA

A partial cDNA, BIT-9, was isolated in a two-hybrid screen using a bait plasmid expressing the cytoplasmic domain of the, integrin subunit. The BIT-9 insert was used to isolate clones from a human placental cDNA library. A 1.8 kb clone, Plac5, was found to contain a high degree of similarity to cDNAs encoding protein kinases, and recognized a widely expressed transcript of 1.8 kb in Northern blots. Deduced amino acid residues 186-451 from Plac5 comprise a domain which is highly homologous with the catalytic domains of a large number of protein tyrosine and serine/threonine kinases. Residues 33-164 comprise four repeats of a motif originally identified in erythrocyte ankyrin, likely defining a domain involved in mediating additional protein-protein interactions. Affinity-purified anti-ILK antibodies (see methods described in Example 3) were used in Western blot analyses of mammalian cell extracts, and detected a conserved protein of apparent Mr of 59 kDa (p59ILK).

Yeast two-hybrid cloning, characterization, and expression of ILK. The full length ILK cDNA, Plac5, was isolated from a human placental library using the BIT-9 insert. Plac5 contains a 1509 bp open reading frame, with a presumptive initiator Met at nt 157, and an AAUAAA signal 11 bp upstream of the polyadenylation site. In vitro transcription and translation of Plac5 in rabbit reticulocyte lysates yielded a protein of apparent Mr of 59 kDa. A search of the PIR protein database indicated homology with protein kinase subdomains I to XI, as identified by Hanks et al. We note sequence variations in the ILK subdomains I, VIb, and VII, relative to catalytic domains of known protein kinases. Subdomain I (residues 199-213), does not have the typical GXGXXG motif, although this region in ILK is Gly-rich. In subdomain VIb, Asp328 of ILK may compensate for the lack of the otherwise conserved Asp319. In subdomain VII, the DFG triplet is absent in ILK. The integrin binding site maps to amino acid residues 293-451 (BIT-9). The ILK kinase domain is most highly related to the CTR1 kinase of *Arabidopsis thaliana* (30% identity, P<10). The CTR1, B-raf, Yes and Csk kinase domains are aligned with Plac5. Amino acid residues 33-164 comprise four contiguous ankyrin repeats, as defined by Lux et. al. BIT-9 was used to probe a blot of poly A+ selected RNA (MTN I, Clontech) from various human tissues. (e) Whole cell lysates of mouse, rat and human cell lines (10 .mu.g/lane) were analyzed by Western blotting with the affinity-purified 92-2 antibody (see description of methods in Example 3). The ILK sequence data are available from GenBank under accession number U40282.

In order to construct integrin "bait" plasmids, sequences encoding amino acid residues 738-798 of the $\beta_1$, and residues 1022-1049 of the $\alpha_5$ integrin subunits were amplified from full-length cDNAs. The primers used were (a) 5' amplification (SEQ ID NO:7) 5'-GGCCGAATTCGCTGGAATTGT-TCTTATTGGC-3' and (b) 3' amplification (SEQ ID NO:8) 5'-GGCCGGATCCTCATTTTCCCTCATACTTCGG-3'.
PCR products were directionally cloned into pEG202, creating the LexA fusion bait plasmids, pEG202$\beta_1$ INT and pEG202$\alpha_5$ INT. pEG202$\beta_1$ INT and pEG202$\alpha_5$ INT repressed β-gal expression from the pJK101 reporter by 50-60% and 70-75%, respectively, in host strain EGY48 (MATα, his3, trp1, ura3-52, LEU2::pLEU2-LexAop6, constructed by Erica Golemis, Massachussetts General Hospital), confirming nuclear expression of the LexA fusions. Co-transformation of baits with the pSH18-34 reporter verified they were transcriptionally inert. A galactose-inducible HeLa cDNA interactor library was present on the TRP+ vector, pJG4-5 (constructed by Jeno Gyuris, MGH). For the $\beta_1$ interaction trap, EGY48 was transformed sequentially with pEG202$\beta_1$ INT, pSH18-34 and pJG4-5, using the lithium acetate protocol (transformation efficiency=5-6×10$^4$/µg). 2×10$^6$ primary transformants were screened, of which forty-nine interacting clones were confirmed. The most frequent isolate (31/49) was a 700 bp insert, BIT-9. Retransformation of EGY48 with the BIT-9, pSH18-34, and pEG202$\beta_1$ INT plasmids resulted in strong β-galactosidase expression, confirming the interaction. An identical screen, using pEG202$\alpha_5$ INT as bait, resulted in the isolation of 16 positives, none of which were represented in the set of 49 $\beta_1$ interactors. Trapped inserts were used to screen WM35 human melanoma λgt10, and human placental λgt11 cDNA libraries, using standard procedures. cDNA sequencing of multiple clones from each library was done using the dideoxy chain termination method (Sequenase 2.0, U.S. Biochemical). For data analysis we used the Genetics Computer Group software package (version 7.0), and database searches were accomplished via the BLAST server at the National Center for Biotechnology Information.

EXAMPLE 2

Analysis of ILK In Vitro

For analysis of kinase activity in vitro, a bacterially-expressed fusion protein, GST-ILK$^{232}$, was SDS-PAGE band purified, and incubated with [γ$^{32}$P]ATP in the presence or absence of the exogenous substrate myelin basic protein. GST-ILK$^{232}$ autophosphorylated and labeled MBP efficiently in these assays. Anti-GST-ILK$^{232}$ (antibody 91-3) immunoprecipitates of PC3 cell lysates were incubated with [γ$^{32}$P]ATP, similar to experiments performed with purified recombinant GST-ILK$^{232}$. ILK immune complexes labeled a protein of apparent Mr of 59 kDa, corresponding to P59$_{ILK}$, as well as cellular proteins of apparent Mr 32 kDa and 70 kDa, which may be endogenous ILK substrates. Cellular phosphoproteins (serine/threonine) of approximately 32 kDa and 70 kDa, were also seen in $\beta_1$ integrin-specific immune complex kinase assays.

In ILK immune complex kinase assays a synthetic peptide representing the $\beta_3$ cytoplasmic domain was phosphorylated, while a similar peptide representing the $\beta_3$ cytoplasmic domain was not detectably labeled by P59$_{ILK}$. The $\beta_1$ peptide selectively inhibited autophosphorylation of ILK in these reactions, further indicating a differential interaction of the peptides with ILK. The results demonstrating phosphorylation of synthetic β peptides by endogenous ILK are identical to those seen with recombinant GST-ILK$^{232}$, and indicate the potential substrate preference of ILK for the $\beta_1$ cytoplasmic tail. This does not, however, necessarily rule out an interaction between ILK and the 3 integrin cytoplasmic domain. Phosphoamino acid analyses of labeled P59$_{ILK}$ and MBP from the immune complex kinase assays detected only phosphoserine in both substrates, as was the case for phosphorylation of these substrates by GST-ILK$^{232}$. The $\beta_1$ peptide was labeled on serine and threonine residues, with approximately equal stoichiometry. As a control, anti-FAK immune complexes from the same lysates were analyzed for phosphorylation of MBP, and phosphotyrosine was readily detected.

In vitro and immune-complex kinase assays. In vitro kinase reactions containing 2 µg of gel-purified GST-ILK$^{232}$, with and without 5 µg of myelin basic protein (MBP, Upstate Biotechnologies, Inc.), were analyzed by 10% SDS-PAGE. Immune complexes were generated from PC3 whole cell lysates, using affinity-purified 91-3 antibody. Complexes were assayed for kinase activity, with and without addition of 5 µg/reaction of synthetic peptides, representing $\beta_1$ or $\beta_3$ integrin cytoplasmic domains or MBP. Products were analyzed by 15% SDS-PAGE, and migration of peptides confirmed by Coomassie Blue staining. $^{32}$P-labeled products from the anti-ILK immune complex kinase reactions, were isolated and analyzed for phosphoamino acid content. Anti-FAK immune complex kinase assays demonstrated phosphotyrosine on MBP.

Protein kinase assays were performed in 50 µl kinase reaction buffer (50 mM HEPES pH 7.0, 10 mM MnC$_2$, 10 mM MgCl$_2$, 2 mM NaF, 1 mM Na$_3$ VO$_4$), containing 10 .mu.Ci [γ$^{32}$P]ATP. Reactions were incubated at 30° C. for 20 min, and stopped by the addition of SDS-PAGE sample buffer. For assay of recombinant ILK activity, GST-ILK$^{232}$ was adsorbed from bacterial lysates onto glutathione-agarose beads, or GST-ILK$^{232}$ was band-purified from 10% SDS-PAGE gels. For immune complex kinase assays, affinity-purified 91-3 anti-ILK antibody was used to generate immunoprecipitates from NP-40 lysates (150 mM NaCl, 1% (v/v) NP-40, 0.5% (w/v) sodium deoxycholate, 50 mM HEPES pH 7.5, 1 µg/ml each leupeptin and aprotinin, 50 µg/ml phenyl-methylsulfonyl flouride) of PC3 cells. Kinase reaction products were resolved on 10-15% SDS-PAGE gels, transferred to PVDF, and phosphoamino acid analysis performed according to a published protocol.

EXAMPLE 3

Association of ILK and B Integrin in Mammalian Cells

Immunofluorescence experiments indicated that ILK and β integrin co-localize in Focal plaques. In order to test further for this association in intact mammalian cells, we performed co-immunoprecipitation assays in lysates of PC3 cells, in which integrin expression has been well-characterized. PC3 cell lysates were immunoprecipitated with specific anti-integrin antibodies, and immune complexes analyzed by Western blotting with the anti-ILK antibody, 92-2. The specificities of the anti-ILK antibodies were tested by immunoprecipitation and Western blotting. We detected P59$_{ILK}$ in immune complexes obtained with anti-fibronectin receptor (FNR, $\alpha_5/\alpha_3$ β integrin), and anti-vitronectin receptor (VNR, $\alpha_v$ $\beta_3/\beta_5$ integrin) antibodies, but not in those obtained with non-immune serum. Three anti-$\beta_1$ monoclonal antibodies also co-precipitated $P59_{ILK}$ from PC3 lysates, confirming the $\beta$ integrin specificity of $P59_{ILK}$ interaction. The detection of $P59_{ILK}$ in anti-VNR immune complexes suggests that ILK may also interact with the $\beta_3$ and/or $\beta_5$ integrin subunit(s).

Antibodies to GST-ILK$^{232}$ recognize $P59_{ILK}$ in integrin co-immunoprecipitations. Unfractionated polyclonal anti-ILK sera 91-3 and 92-2 specifically recognize a $^{35}$S-methionine, metabolically-labeled cellular protein, of apparent Mr of 59 kDa. Affinity-purified 92-2 antibody was adsorbed with 165 µg of agarose-coupled GST-ILK$^{232}$, or agarose-GST, which preparations were used in parallel Western blots containing 10 µg/lane of whole cell lysates of PC3 cells, Jurkat T-lymphoblasts, or the 60 kDa GST-ILK$^{232}$. Polyclonal anti-integrin antibodies, specific for the fibronectin and vitronectin receptors, were used to precipitate surface-biotinylated integrins from PC3 cells, and immune complexes were then analyzed for the presence of $P59_{ILK}$, by Western blotting with affinity-purified, biotin-labeled 92-2 antibody. This result is representative of six independent experiments. Anti-$\beta_1$ monoclonal antibodies were used in co-precipitation analyses of NP-40 lysates of PC3: lane 1, A.sub.II B$_2$; lane 2, anti-CD29; lane 3, 3S3. Western blotting of anti-$\beta_1$ immune complexes with affinity-purified, biotinylated 92-2 antibody (left). This blot was stripped and reprobed with the same concentration of biotinylated 92-2, adsorbed against an excess of GST-ILK$^{232}$ beads. We observe co-precipitation of $P59_{ILK}$ using a panel of 11 anti-$\beta_1$ monoclonals, but not with an anti-CD44 monoclonal antibody. The migration of $P59_{ILK}$ was confirmed in parallel lanes containing PC3 whole cell NP-40 lysates. Markers at left, in kDa.

Amino acid residues 132-451 of ILK were expressed as a GST fusion protein, in *E. coli*. Recombinant GST-ILK$^{232}$ protein was purified and used to inject two rabbits. The resulting antisera, 91-3 and 92-2 (raised by Research Genetics, Inc.), were affinity-purified over a column of CNBr-Sepharose coupled GST-ILK$^{232}$. PC3 cells were metabolically labeled with 100 µCi/ml [35S]methionine/[$^{35}$S]cysteine ([$^{35}$S] ProMix, 1000 Ci/mmol, Amersham), for 18 hours in cysteine/methionine-free MEM. For co-immunoprecipitation experiments PC3 cells were surface-labeled with sulfo-NHS-biotin (Pierce Chemicals), prior to lysis in NP-40 buffer. Polyclonal anti-fibronectin receptor (anti-FNR, Telios A108), and anti-vitronectin receptor (anti-VNR, Telios A109) antibodies were purchased from Gibco/BRL. 1-2 mg of NP40 lysate was incubated at 4° C., with 2-3 µl/ml anti-FNR or anti-VNR antiserum, or 2 µg/ml of the anti-$\beta_1$ monoclonal antibodies A.sub.II B$_2$ (C. Damsky, UC, San Francisco), anti-CD29 (Upstate Biotechnology, Inc.), and 3S3 (J. Wilkins, U Manitoba). Lysates were pre-cleared and immune complexes collected with Protein A-Sepharose. For Western blotting, RIPA lysates or immune complexes were subjected to 7.5% or 10% SDS-PAGE, and proteins then electrophoretically transferred to polyvinylidene fluoride membranes (Immobilon-P, Millipore). Membranes were blocked in 5% non-fat milk/Tris-buffered saline Tween-20, and incubated with 0.5 µg/ml affinity purified antibodies. Horseradish peroxidase-coupled goat anti-rabbit IgG was used in secondary incubations, followed by detection of reactive bands by enhanced chemiluminescence (ECL, Amersham). For blotting without use of secondary antibody, affinity-purified 92-2 antibody was labeled with Biotin Hydrazide (Immunopure, Pierce Chemicals), according to the manufacturer's protocol, with visualization by peroxidase-conjugated streptavidin (Jackson ImmunoResearch Laboratories) and ECL. For re-probing, membranes were stripped according to manufacturer's instructions.

EXAMPLE 4

Overexpression of ILK Provides Growth Advantage

The fibronectin-dependent regulation of ILK kinase activity was tested. Plating of rat intestinal epithelial cells, IEC-18 on fibronectin reduced ILK phosphorylation of MBP in immune complex kinase assays, relative to cells plated on plastic, or kept in suspension. This fibronectin-dependent reduction of ILK activity was abrogated in IEC-18 cells expressing an activated H-ras allele, indicating that ras transformation disrupts ECM regulation of ILK activity in these cells. An expression vector containing the full-length ILK cDNA, pCMV-ILK, was stably transfected into IEC-18 cells. Twelve stable clones each, of pCMV-ILK and vector control transfectants, were selected and characterized for $P59_{ILK}$ expression levels. Two representative overexpressing subclones, ILK13-A1a3 and -A4a are illustrated. Overexpression of $P59_{ILK}$ disrupted the epithelial morphology of IEC-18 cells. ILK13 clones were more refractile, and grew on LN, FN and VN with a stellate morphology, in marked contrast to the typical, "cobble-stone" morphology of the parental and ILK14 cells. We plated the ILK13-A1a3 and -A4a subclones, the control transfectants, ILK14-A2C3 and -A2C6, and IEC-18 cells, on varying concentrations of the integrin substrates, laminin (LN), fibronectin (FN) and vitronectin (VN). Adhesion of the ILK14 and IEC-18 cells was equivalent, whereas that of the overexpressing subclones was significantly reduced, on all these substrates. Immunoprecipitation analysis indicated that cell surface integrin expression was unaffected. The effect of $P59_{ILK}$ overexpression on anchorage-independent growth was examined by assaying the colony forming ability of ILK transfectants in soft agarose. In marked contrast to IEC-18 and transfectant controls, four independent $P59_{ILK}$ overexpressing subclones, ILK13-A4a, A1a3, A4d3 and A4C12, formed colonies in these assays. The proliferative rates of all of these clones on tissue culture plastic were equivalent to control rates.

Modulation of ILK kinase activity by ECM components. ILK phosphorylation of MBP was assayed in ILK immune complexes, from lysates of IEC-18 intestinal epithelial cells which were harvested from tissue culture plastic and either kept in suspension, or replated on fibronectin, for 1 hour. A H-ras-transformed variant of IEC-18, Ras37 (transfected with Rasval12 in pRC/CMV vector), was assayed in parallel. The band shown is MBP. b, Expression levels of $P59_{ILK}$ in two representative clones of IEC-18 cells, transfected with an ILK expression construct (ILK13), two vector control clones (ILK14), and the parental IEC-18 cells are presented. The indicated amounts of whole cell RIPA lysates were run out on 10% SDS-PAGE gels, and $P59_{ILK}$ expression analyzed by Western blotting with affinity-purified 92-2 antibody. Representative $P59_{ILK}$ overexpressing clone ILK13-A4a, vector control clone ILK14-A2C3, and parental. IEC-18 cells were plated on the ECM substrates LN, FN and VN for 1 hour, then fixed, stained with toluidine blue and photographed (40Xmag). Adhesion of the ILK overexpressing clones to LN, FN and VN was quantified. Key: IEC-18 (black), ILK14-A2C6 (white), ILK13-A1a3 (dark grey), ILK13-A4a (light grey). Results are presented for 10 µg/ml substrate, and are expressed as % adhesion (+/−s. d.) relative to IEC-18, for each substrate. The serial concentrations of ECM showed similar reductions in adhesion of the ILK13 subclones, and ILK14-A2C3 adhesion was identical to that of ILK14-A2C6, on all three substrates. Immunoprecipation of surface-biotinylated IEC-18, ILK13, and ILK14 subclones, with the anti-FNR and anti-VNR sera, confirmed there was no change in expression of $\alpha_5/\alpha_3$ $\beta_1$ and $\alpha_v$ $\beta_3/\beta_5$ integrin subunits in the $P59_{ILK}$ overexpressors. Data are representative of two independent experiments. Four ILK13, $P59_{ILK}$ overexpressing clones were plated in soft agarose, and assayed for colony growth after three (experiment 1) and two (experiment 2) weeks. Parent and vector control transfectants were also assayed, and the ras val12 transformed clone, Ras-37, was used as a positive control. Bars represent the mean of duplicate determinations. Maximum colonies in IEC-18 and ILK14 cells was 1/field.

The rat intestinal epithelial cell line IEC-18, and a variant of this line transfected with an activated H-rasval12 allele, expressed from pRC/CMV, were grown on tissue culture plastic in 5% serum-containing medium, washed three times in minimum essential medium (MEM), and harvested with 5 mM EDTA. These were resuspended in 2.5 mg/ml BSA in MEM, and either kept in suspension, or plated on 10 □g/ml fibronectin-coated plates, for 1 hour at 37° C. NP-40 lysates (300 μg) of these cells were immunoprecipitated with affinity-purified 91-3, and immune complex kinase assays (MBP substrate) performed, as described above. IEC-18 were transfected with the expression vector pRC/CMV, containing Plac5 in the forward orientation relative to the CMV promotor. Stable clones were selected in G418, and subcloned through two rounds of limiting dilution. In all, twelve each of ILK and vector control transfectant subclones were isolated. Protein concentrations were determined using the Bradford reagent (Bio-Rad). Two $P59_{ILK}$ overexpressors, ILK13-A1a3 and ILK13-A4a, and two vector transfectant controls, ILK14-A2C3 and -A2C6, were analyzed for effects of ILK overexpression on cell adhesion to ECM substrates. Adhesion was quantified according to published methods. For colony formation assays $3\times10^5$ cells were plated in 35 mm wells, in 0.3% agarose, as described previously. Ras-37 were plated at $2\times10^3$/well. Colonies were counted and scored per field (d=1 cm) in duplicate wells, and defined as a minimum aggregate of 50 cells.

These results demonstrate that $P59_{ILK}$ overexpression in the IEC epithelial cells provides a growth advantage, in the absence of proliferative signals normally provided by adhesion.

The transduction of extracellular matrix signals through integrins influences intracellular ('outside-in') and extracellular ('inside-out') functions, both of which appear to require interaction of integrin cytoplasmic domains with cellular proteins. The association of ILK with $\beta_1$ integrin subunits, and specific regulation of its kinase activity by adhesion to fibronectin, suggests that $P59_{ILK}$ is a mediator of integrin signaling. Thus the ankyrin repeat motif likely represents a protein interaction module specifying interactions of ILK with downstream, cytoplasmic or cytoskeletal proteins. Reduced ECM adhesion by the $P59_{ILK}$ overexpressing cells is consistent with our observation of adhesion-dependent inhibition of ILK activity, and suggests that $P59_{ILK}$ plays a role in inside-out integrin signaling. Furthermore the $P59_{ILK}$-induced, anchorage-independent growth of epithelial cells indicates a role for ILK in mediating intracellular signal transduction by integrins.

EXAMPLE 5

The Effect of Anti-ILK on Cell Migration

The role of ILK in cell motility has important implications for normal physiological processes such as inflammation and wound healing, as well as pathological conditions involving tumour invasiveness and metastatic tumour spread, or osteoporosis (bone is essentially an extracellular matrix secreted by osteoblast, or bone-forming cells, and this deposition can be modulated by integrin expression levels and function). Cell motility is a dynamic process, which is dependent on integrin-ECM interactions. The "on-off" switch function of protein kinases provides an ideal mechanism for the dynamic regulation of integrin affinity states for ECM substrates. The effect on cell migration of microinjecting highly specific anti-ILK antibodies (thereby inhibiting ILK function) into the cell's cytoplasm is assayed. These effects are assayed in endothelial cells plated on solid substrata, and are extended to include studies on cell migration through three-dimensional gels composed of ECM proteins.

EXAMPLE 6

Anti-Sense Oligonucleotides to Inhibit ILK Activity

The sequence of ILK cDNA provides information for the design and generation of synthetic oligonucleotides for "anti-sense" inhibition of ILK activity. This term derives from the strategy of employing a reverse complement of the coding, or sense strand of a specific messenger RNA, known as an anti-sense oligonucleotide (AO). By binding to its complementary mRNA, the AO inhibits translation of that mRNA into protein, thereby preventing normal protein accumulation in the cell. ILK AO derived from the ILK mRNA sequence closest to the presumptive translational start site is tested, as this is predicted to provide the most successful reagent.

Regardless of the actual chemistry used to construct the AO, or modifications to an anti-ILK AO to improve its efficiency, the cDNA sequence of ILK provides the information for derivation of a specific AO. The cDNA sequence of ILK is also used to design oligonucleotide reagents, known as degenerate primers (due to the degeneracy of the genetic code), for use in polymerase chain reaction (PCR)-based screens for cDNAs structurally related to ILK. Similarly, the ILK cDNA is used to screen for related genes in a more conventional screen of genomic or cDNA libraries, by employing less stringent (i.e. milder) hybridization conditions during screening. In this way, distinct cDNA or DNA sequences significantly related to ILK (>50% nucleotide identity) can be isolated, and a family of ILK-related kinases identified in a non-random fashion.

EXAMPLE 7

Mapping of ILK Chromosomal Locus to Assess Imprinted Copies of Gene

High resolution mapping of the ILK chromosomal locus through fluorescent in situ hybridization (FISH) to metaphase (i.e. separated and identifiable) human chromosomes has placed the ILK gene on chromosome 11p15. FISH is known to those skilled in the art. High resolution mapping uses known marker genes in this region. Certain genes (e.g. insulin-like growth factor 2, IGF2) in the 11p15 region have been shown to be imprinted (i.e. preferentially expressed from either the maternally or paternally-derived chromosomes). This imprinting effectively provides a functional deletion or "knock-out" of one of the two inherited copies of a gene. Thus, mutation of the non-imprinted allele (copy) has a more profound outcome, since no compensatory activity is available from the imprinted allele. Also, 11p15 has been identified as a region subject to loss-of-heterozygosity, or LOH, in a subset of breast tumour patients. LOH results in the loss of one allele, for example by gene deletion, and is a mechanism underlying the contribution of a number of tumor suppressor genes to the development of various cancers (e.g. BRCA1 in breast, DCC in colon carcinoma, and RB1 in retinoblastoma). Thus ILK cDNA sequence is used to develop DNA reagents for the diagnosis and prognostic indications of a significant subset of breast cancers, and these reagents contribute to the molecular classification of such tumors. As mentioned above, the gene(s) on 11p15 contributing to some inherited cases of long QT syndrome are identified, and the candidacy of ILK as a causative gene for this cardiac condition, are evaluated by looking for alterations in ILK gene structure in families where 11p15 associations have been made.

EXAMPLE 8

Induction of In Vivo Tumorigenesis by Overexpression of ILK

Overexpression of ILK down-regulates E-cadherin which is an important epithelial cell adhesion molecule mediating cell-cell communication/interaction. The loss of E-cadherin induced by overexpression of ILK in epithelial cells suggests that ILK may promote tumorigenicity in vivo. To test this, we injected cells expressing varying levels of ILK into athymic nude mice subcutaneously. Mice were inoculated subcutaneously with the cells expressing high (ILK13-A1a3 and A4a) or low (IEC-18 and ILK14-A2C3) levels of ILK ($10^7$ cells/mouse in PBS). The mice were monitored for tumor formation at the site of inoculation after three weeks. Tumors arose within three weeks in 50% to 100% of the mice injected with the ILK13 cells (10.sup.7 cells/mouse) that overexpress ILK, whereas no tumors were detected in the mice that were injected with the same number of the IEC-18 or ILK14 cells expressing lower levels of ILK (Table 1). Thus, overexpression of ILK in these epithelial cells promotes tumor formation in vivo.

TABLE 1

Tumorigenicity of ILK Overexpressing IEC-18 Cells

| Cell Line | Number of Mice with Tumors at 3 weeks |
|---|---|
| IEC-18 | 0/6 |
| ILK14-A2C3 | 0/6 |
| ILK13-A1a3 | 6/6 |
| ILK13-A4a | 3/6 |

EXAMPLE 9

Increased Expression of ILK in Human Breast Carcinoma

The expression of Integrin Linked Kinase in human breast carcinomas was determined by immunohistochemical staining of paraffin embedded sections from human breast cancer biopsies. Affinity purified anti-ILK polyclonal antibody was used followed by conjugated secondary antibody. The positive staining observed was completely abolished by absorption of the antibody to ILK-coupled sepharose beads. A total of 30 samples have been examined so far. In every case ILK expression levels are markedly elevated in tumor tissue compared to normal ducts and lobules. A normal region showing well formed ducts with a single layer of epithelial cells. ILK staining is most prominent in epithelial cells. The stroma appears negative. Ductal carcinoma in situ (DCIS). Multiple cell layers are present with markedly elevated ILK staining in the tumor cells. Invasive carcinoma has markedly elevated expression of ILK compared to the normal tissue.

EXAMPLE 10

Regulation of LEF-1 Expression and Complex Formation

Overexpression of ILK results in a downregulation of E-cadherin expression, formation of a complex between β-catenin and the HMG transcription factor, LEF-1, translocation of β-catenin to the nucleus, and transcriptional activation by this LEF-1/β-catenin complex. LEF-1 protein expression is rapidly modulated by cell detachment from the extracellular matrix, and that LEF-1 protein levels are constitutively upregulated upon ILK overexpression. These effects are specific for ILK, since transformation by activated H-ras or v-src oncogenes do not result in the activation of LEF-1/β-catenin. The results demonstrate that the oncogenic properties of ILK involve activation of the LEF-1/β-catenin signaling pathway via elevation of LEF-1 expression.

Overexpression of ILK in rat intestinal epithelial cells (IEC-18) induces a loss of epithelial morphology, characterized by a disruption of cell-cell adhesion and the acquisition of a fibroblastic morphology that includes enhanced fibronectin matrix assembly. This altered morphology is accompanied by the ability of the cells to progress through the cell cycle in an anchorage-independent manner and to form tumors in nude mice. To determine whether the loss of cell-cell adhesion was accompanied by an increased invasive phenotype, the invasiveness of IEC-18 parental cells and ILK-overexpressing (ILK-13) cells was tested in a collagen gel invasiveness assay. The data is shown in Table 2.

The ILK-13 cells are much more invasive than the parental and control transfected (ILK-14) cells that have been transfected with an ILK anti-sense cDNA construct. Collagen-gel invasion by epithelial cells is normally associated with an epithelial to mesenchymal transformation characterized by the down regulation of E-cadherin expression. Notably, the expression of E-cadherin protein is completely lost in ILK overexpressing cells (ILK-13), but is maintained in control transfected cells, reduced in IEC-18 cells transfected with activated H-ras cDNA, and greatly reduced in v-src transformed cells. In contrast, the steady-state levels of the expression of the intracellular E-cadherin binding protein, β-catenin, is unchanged by ILK overexpression and is similar in all IEC cell transfectants.

The subcellular localization of β-catenin was examined in these cells. In sharp contrast to the localization of β-catenin at the plasma membrane and at cell-cell adhesion sites in the parental IEC-18 and control transfected cell clones (A2c3 and A2c6), β-catenin is localized entirely in the nuclei of ILK overexpressing ILK-13 clones (A4a, A1a3). This ILK-induced nuclear localization of β-catenin is dependent on an active kinase, since overexpression of a kinase-deficient ILK (E359K) did not induce nuclear translocation of β-catenin which remains localized largely to the plasma membrane. Likewise, overexpression of kinase-deficient ILK also did not result in a loss of E-cadherin expression. The translocation of β-catenin to the nucleus is a specific property of ILK, since in IEC-18 cells transfected with activated H-ras or v-src oncogenes, β-catenin is not translocated to the nucleus, but is either localized to the plasma membrane or is expressed diffusely in the cytoplasm. Although these oncogenes also disrupt the epithelial morphology of IEC-18 cells and result in the downregulation of E-cadherin expression, the translocation of β-catenin to the nucleus is a property unique to ILK expression, suggesting that loss of E-cadherin expression and β-catenin nuclear translocation may be regulated differentially. Overexpression of ILK in mouse mammary epithelial cells also results in similar alterations in the phenotypic properties described above for the IEC-18 cells.

Translocation of β-catenin to the nucleus can be induced by the activation of the Wnt signaling pathway, which initially results in an elevation of free cytosolic β-catenin due to decreased degradation. Alternatively, loss of expression or mutations in the tumor suppressor protein APC and certain mutations in the β-catenin gene lead to cytosolic β-catenin stabilization and nuclear translocation. The nuclear translocation of β-catenin is associated with complex formation between β-catenin and members of the HMG transcription factors, LEF-1/TCF which then activate (or silence) transcription of target genes. Since the steady state levels of β-catenin were not changed by ILK overexpression "uncomplexed" β-catenin levels were measured, as determined by binding to a cytoplasmic domain peptide of E-cadherin. "Uncomplexed" pools of β-catenin in ILK overexpressing clones were found to be low and unaltered compared to IEC-18 cells or control ILK 14 clones. This indicates that most β-catenin is likely complexed with nuclear components such as transcription factors and DNA. In contrast, free β-catenin pools in Ras and Src transformed cells were high consistent with decreased E-cadherin expression and indicating disruption of E-cadherin-β-catenin interaction. However, the increased free pools of β-catenin did not result in nuclear translocation of β-catenin.

The expression levels of LEF-1, a member of the family of HMG transcription factors that bind β-catenin, were measured. The expression of LEF-1 is dramatically higher in six independent ILK expressing ILK-13 cell clones as compared with six independent control transfected ILK-14 clones, as well as 2 activated H-ras transfected and v-src transfected IEC-18 clones. E-cadherin expression is lost in all 6 ILK-13 cell lines. Transient induction of ILK expression using an ecdysone inducible ILK construct also resulted in an increase of LEF-1 expression. As expected, the increased levels of LEF-1 and the nuclear translocation of β-catenin are associated with enhanced complex formation between LEF-1 and β-catenin in the ILK overexpressing cells.

LEF-1 is a transcription factor that is by itself, unable to stimulate transcription from multimerized binding sites, however in association with β-catenin, LEF1/TCF proteins can augment promoter activity from multimerized binding sites. Transcriptional activation from a TCF/β-catenin responsive promoter construct was examined in ILK-overexpressing cells and control kinase-deficient ILK expressing cells. High promoter activity was observed in ILK-overexpressing cells and the extent of transcriptional activation was reduced with promoter constructs containing mutations in the multimerized LEF-1/TCF binding sites. Moreover, nuclear extracts were analyzed from ILK-overexpressing cell clones and from cell clones transfected with an anti-sense or kinase-deficient ILK cDNA to identify proteins that bind the LEF/TCF binding site. The abundance of a nuclear factor in ILK-overexpressing cells that displays the same binding site specificity, immunoreactivity and electrophoretic mobility as LEF-1, was found to be markedly enhanced relative to the unrelated DNA-binding protein Oct-1.

ILK binds to the cytoplasmic domain of $\beta_1$ and $\alpha_3$ integrin subunits, and its kinase activity is downregulated upon cell adhesion to extracellular matrix (ECM) proteins. Overexpression of constitutively activated ILK overcomes this regulation of ILK activity by integrin occupation and results in decreased cell adhesion to ECM-protein. Cell adhesion to ECM suppresses LEF-1 expression, which is rapidly, but transiently, elevated upon cell detachment in ILK-14 and ILK13 cells. However in ILK overexpressing ILK-13 cells the elevation in LEF-1 levels are more robust and are maintained at high levels for as long as 16 hours in suspension. Furthermore, LEF-1 levels are also higher in adherent ILK-13 cells compared to ILK-14 cells.

These data indicate that ILK overexpression overcomes the regulation of LEF-1 expression by adhesion-deadhesion, and that the maintenance of constitutively high levels of LEF-1 result in enhanced complex formation between LEF-1 and β-catenin, translocation of β-catenin to the nucleus, and transcriptional activation of responsive genes. Since TCF/β-catenin has been shown to induce transcription of genes encoding homeobox proteins that regulate mesenchymal genes eg. Siamois in *Drosophila*, this pathway is likely to mediate the observed epithelial to mesenchymal transformation, as well as the oncogenic properties of ILK in these intestinal epithelial cells, since constitutive activation of TCF/β-catenin is oncogenic in human colon carcinomas. The data presented here also suggest a connection between the expression of E-cadherin and the signaling properties of β-catenin in mesenchymal induction in ILK transformed cells, in agreement with the work of others that E-cadherin can antagonize β-catenin signaling, although the loss of E-cadherin expression does not always correlate with, nuclear β-catenin translocation e.g. in the v-src transformed cells.

An additional pathway is demonstrated to that by activated Wnt-1 leading to increased LEF-1/β-catenin complex formation and transcriptional activation. These data also corroborate previous work showing that overexpression of LEF-1 can work independently of Wnt to enhance LEF-1-β-catenin complex induced transcription. Here it is shown that in contrast to the effects of Wnt-1, activated ILK can dramatically induce the formation and nuclear translocation of LEF-1/β-catenin complexes without a corresponding increase in the free pool of β-catenin. This ILK-regulated pathway may be modulated via cell adhesion to ECM, but can be constitutively activated by ILK overexpression.

Methods

Cells and cell culture. IEC-18 rat intestinal epithelial cells were stably transfected with a mammalian vector incorporating ILK to produce clones overexpressing wt ILK in the sense orientation (ILK-13) or antisense orientation (ILK-14), or to produce a kinase-deficient form of ILK (IEC-18 GH31RH) described below. IEC-18 cells were also stably transfected to overexpress H-ras (Ras 33, Ras 37) (Buick et al. (1987) Exp. Cell. Res. 170:300-309), and v-src (Src2, Src4) (Filmus et al. (1988) Mol. Cell. Biol. 8:4243-4249). Cells were grown in d-MEM containing 5% FCS, 2 mm L-glutamine, glucose (3.6 mg/ml), insulin (10 ug/ml), and G418 (40 ug/ml) was added to transfected cells to maintain selection pressure.

Site directed mutagenesis of ILK kinase domain. Mutations were introduced into wt ILK-cDNA with the Promega Altered Sites II System (Promega, Madison Wis.). Mutant oligomers (with the altered nucleotide underlined) were used to change lysine at position 220 to an arginine (K220R, (SEQ ID NO:9) 5'CCTTCAGCACCCTCACGACAATGTCAT-TGCCC 3') and glutamic acid at position 359 to lysine (E359K, (SEQ ID NO:10) 5' CTGCAGAGCTTTGGGGGC-TACCCAGGCAGGTG 3'). Mutant clones were confirmed by dideoxy sequencing and subcloned into pGEX4T-1 GST fusion vector (Pharmacia, Piscataway N.J.) to express GST-ILK in *E. coli* (BL21-DE3) and into pcDNA3 (Invitrogen, San Diego, Calif.) to stably transfect kinase-deficient ILK into the IEC-18 cell line (IEC-18 GH31RH containing the E359K mutation).

Inducible expression of ILK. Full length wt ILK cDNA (1.8 Kb) was subcloned into the Ecdysone-inducible expression vector pIND (Invitrogen, San Diego, Calif.) and 10 ug were transiently co-transfected with 10 ug of the complementary regulator vector pVgRXR into subconfluent cells growing in 6 well plates with 20 ul of Lipofectin (Gibro-BRL, Gaithersburg, Md.). ILK expression was induced 6 hrs later with the addition of 1 uM muristerone A.

Western blotting and immunoprecipitation. Cells were lysed for 10 minutes on ice in NP-40 lysis buffer (1% NP40, 50 mM Hepes, pH 7.4, 150 mM NaCl, 2 mM EDTA, 2 mM PMSF, 1 mM Na-o-vanadate, 1 mM NaF, 10 ug/ml aprotinin, 10 ug/ml leupeptin). Extracts were centrifuged with the resulting supernatants being the cell lysate used in assays. Lysates were electrophoresed through SDS-PAGE and transferred to Immobilon-P membranes (Millipore, Bedford, Md.). Antibodies used to probe Western blots were: rabbit anti-ILK, monoclonal anti-E-cadherin and monoclonal anti-β-catenin (Transduction Labs, Lexington, Ky.), and rabbit anti-LEF-1 (Travis et al. (1991) Genes & Development 5:880-894). Bands were visualized with ECL chemiluminescent substrate (Amersham, Buckinghamshire, England). For immunoprecipitation, NP-40 lysates were rotated with primary antibody ON at 4° C., then rotated with Protein G-Sepharose (Pharmacia, Uppsala, Sweden) for 2 hrs at RT. Beads were pelleted, boiled in electrophoresis sample buffer (non-reducing), centrifuged and supernatants were electrophoresed. Protein concentrations were determined by the Bradford assay (Bio-Rad, Hercules, Calif.).

Invasion assay. Confluent cells were trypsinized and $7.5 \times 10^4$ cells in 1.5 ml of complete medium were seeded onto 1.5 ml of a three dimensional collagen gel in a 35 mm tissue culture dish (Montesano et al. (1985) Cell 42:469-477). Upon reaching confluence (3 days), the cultures were incubated for a further 4 days, then fixed in situ with 2.5% glutaraldehyde in 100 mM cacodylate buffer (pH 7.4), and photographed at different planes of focus. Invasion was quantitated by counting the number of cells which had migrated below the surface of the collagen gel. Five randomly selected fields measuring 1.0 mm×1.4 mm were photographed at a single level beneath the surface monolayer using a 10× phase contract objective.

Indirect immunofluorescence. Cells were grown on cover slips, washed with PBS, fixed in 4% paraformaldehyde in PBS for 12 minutes, washed with PBS, permeabilized in 0.1% Triton X-100 in PBS for 10 minutes, blocked with 4% BSA in PBS for 30 minutes at RT, incubated with rabbit anti-β-catenin (Hulsken et al. (1994) J. Cell Biol. 127:2061-2069) diluted 1:400 in 0.1% Triton X-100 for 60 minutes at 37° C., washed with PBS, incubated with rhodamine conjugated goat anti-rabbit IgG (Jackson ImmunoResearch, West Grove, Pa.) diluted 1:50 in 0.1% Triton X-100 for 30 minutes at 37° C., washed with PBS, then mounted onto a slide with Slow-Fade Antifade (Molecular Probes Inc., Eugene, Oreg.). Cells were viewed at 100 fold magnification using a Zeiss Axiovert 135 fluorescence microscope.

Reportergene assay. Cells were transiently transfected with 0.3 ug of a luciferase reporter gene construct containing a series of optimal or mutated LEF-1/TCF binding sites (Korinek et al. (1997) Science 275:1784-1787), along with 0.05 ug of a CAT gene construct containing a ribosomal promoter (Hariharan et al. (1989) Genes & Development 3:1789-1800) to control for transfection efficiency. Extracts were prepared and assayed 48 hours after transfection.

Electrophoretic mobility shift assay. Twenty μg of nuclear extract were incubated with 1 fmole of $^{32}$P-labeled duplex oligonucleotide probe specific for LEF-1, in 20 μl of binding buffer containing 200 ng poly[d(I-C)], 400 ng salmon sperm DNA, and electrophoresed through a 5% native polyacrylamide gel (Travis et al. (1991) Genes and Development 5:880-894). For DNA competition, an 800-fold molar excess of oligonucleotide containing a specific LEF-1 binding site or a non-specific EBF-binding site (Hagman et al. (1991) EMBO J. 10:3409-3417) was included in the DNA-binding reaction. For antibody addition, 1 ul of polyclonal anti-LEF-1 antibody or 1 ul of monoclonal anti-β-catenin antibody (Transduction Labs, Lexington, Ky.) were used.

TABLE 2

INVASION OF COLLAGEN GELS

| Cell Line | Invading cells/field |
|---|---|
| IEC-18 | 10 +/− 0.87 |
| ILK14/A2c | 67.8 +/− 1.32 |
| ILK13/A1a | 326.73 +/− 2.61 |
| ILK-13/A4a | 83.6 +/− 4.68 |

After seeding $7.5 \times 10^4$ cells, the number of invading cells in 5 photographic fields from 3 separate experiments (total of 15 fields/cell line) were counted. Results are given as the mean number of invading cells +/−SEM. *$p \ll 0.01$ between ILK13/A1a3 compared to IEC-18 and ILK-14 cells (Students unpaired t=test).

Example 11

Regulation of Fibronectin Matrix Assembly, E-cadherin Expression and Tumorigenicity A common feature of many oncogenically transformed cells is that they lose the ability of assembling a fibronectin (Fn) matrix. However, exceptions to the rule of neoplastic cells lacking Fn matrix clearly exist. For example, Fn matrix assembly is dramatically enhanced in hairy cell leukemia cells. The specific phenotype (inhibition or stimulation of Fn matrix assembly) is probably determined by the origin of the neoplastic cells and the initial target of the oncogenic transformation. Because Fn matrix has a major impact on cell adhesion, migration, cell growth and cell differentiation, an understanding of the molecular mechanism by which cells control Fn matrix assembly may provide important information on tumorigenicity and may lead to new ways of controlling tumor growth.

Binding of Fn by specific integrins is critical in initiating Fn matrix assembly. Fn fragments containing the RGD-containing integrin binding site or antibodies recognizing the integrin binding site inhibit Fn matrix assembly. In addition, antibodies to $\alpha_5 \beta_1$ integrin reduce the deposition of Fn into extracellular matrix by fibroblasts. In addition to $\alpha_5 \beta_1$ integrin, members of the $\beta_3$ integrins ($\alpha.\text{sub.IIb} \beta_3$ and $\alpha.\text{sub.v}$ β₃) also initiate Fn matrix assembly, although some of the other Fn binding integrins such as $\alpha_4 \beta_1$ or $\alpha.sub.v \beta_1$ do not. The ability of cells to use multiple integrins to support Fn matrix assembly provides the cells with a versatile mechanism for control of Fn matrix assembly. It may also explain why certain cells, such as fibroblastic cells derived from $\alpha_5$ integrin null mutant embryos, assemble a Fn matrix in the absence of $\alpha_5 \beta_1$. The primary role of $\alpha_5 \beta_1$ in Fn matrix assembly appears to involve initiating the assembly, as Fn mutants lacking the $\alpha_5 \beta_1$ integrin binding site could not be assembled into Fn matrix unless in the presence of native Fn.

Activation of specific Fn binding integrins, either by mutations at the integrin cytoplasmic domains or using activating antibodies, dramatically stimulates Fn matrix assembly. The ability of a cell to assemble a Fn matrix is not only controlled by the types of integrins it expresses but also regulated by the Fn binding activity of the integrins. The extracellular ligand binding affinity of integrins can be controlled from within the cells (inside-out signaling).

Integrin-linked kinase (ILK) may be involved in regulating Fn matrix assembly. ILK binds to the cytoplasmic domains of both $\beta_1$ and $\beta_3$ integrins, and phosphorylates the $\beta_1$ cytoplasmic domain in vitro. Overexpression of ILK in epithelial cells dramatically stimulated integrin-mediated Fn matrix assembly, down-regulated E-cadherin, and induced tumor formation in vivo. The data identify ILK as an important regulator of pericellular Fn matrix assembly, and suggest a critical role of this integrin-linked kinase in cell-cell interactions and tumorigenesis.

Reagents

All organic chemicals were of analytic grade and were obtained from Sigma Chemical Co. (St. Louis, Mo.) or Fisher Scientific Co. (Pittsburgh, Pa.) unless otherwise specified. Media for cell culture were from Gibco Laboratories (Grand Island, N.Y.). Fetal bovine serum was from HyClone Laboratories, Inc. (Logan, Utah). Polyclonal rabbit anti-$\alpha_5$ integrin cytoplasmic domain antibody AB47 was generated using a synthetic peptide representing the membrane distal region of the $\alpha_5$ integrin cytoplasmic domain ((SEQ ID NO:11) LPYGTAMEKAQLKPPATSDA). Polyclonal rabbit anti-Fn antibody MC54 was raised against purified plasma Fn and purified with a protein A-Sepharose affinity column (Wu et al. (1993) J. Biol. Chem. 268:21883-21888). Polyclonal rabbit anti-29 kDa fragment of Fn antibody was raised against the aminoterminal 29 kDa fragment of Fn and was further purified using Sepharose beads coupled with the 29 kDa fragment of Fn (Limper et al. (1991) J. Biol. Chem. 266:9697-9702). Anti-ILK polyclonal antibody 91-4 was prepared in rabbits as described previously (Hannigan et al. (1996) Nature 379:91-96). Monoclonal hamster anti-rat α5 integrin antibody (HMα5-1) and mouse anti-rat β₃ integrin antibody. (F11) were from PharMingen (San Diego, Calif.). Monoclonal mouse anti-vinculin antibody (hVIN-1) and purified rabbit IgG were purchased from Sigma (St. Louis, Mo.). The Fn fragments (110 kDa RGD containing integrin binding fragment, the 20 kDa and 70 kDa amino terminal fragments, and the 60 kDa gelatin binding were prepared as previously described (Quade and McDonald (1988) J. Biol. Chem. 263: 19602-19609). cDNA Vectors, Transfection and Cell Culture. Rat intestinal epithelial cells (IEC-18) were maintained in α-MEM medium (Gibco Laboratories, Grand Island, N.Y.) supplemented with 5% FBS (Atlanta Biologicals, Norcross, Ga.), 3.6 mg/ml glucose, 10 μg/ml insulin and 2 mM glutamine. The pRC/CMV and metallothionein promoter (MT) driven expression vectors containing sense and anti-sense full length ILK cDNA sequences were generated as described above. The expression vectors were transfected into IEC-18 cells using calcium phosphate and the transfected cells were selected with G418 as described. The expression of human ILK in IEC-18 cells transfected with the MT-ILK expression vectors (MT-ILK) was induced by growing the cells in α-MEM medium containing 125 μM $ZnSO_4$ and 2.5 μM $CdCl_2$ for 24 to 48 hours. The kinase-inactive ILK mutant (GH31R) was generated by a single point mutation (E.fwdarw.K) at amino acid residue 359 within the kinase subdomain VIII using the Promega Altered Site II in vitro Mutagenesis System. The mutated DNA was cloned into a pGEX expression system (Pharmacia), and expressed as a GST fusion protein. Kinase assays were carried out using the recombinant protein as described above and the results showed that the $E^359$.fwdarw.K point mutation completely inactivated the kinase activity. The cDNA encoding the kinase-inactive mutant was cloned into a pcDNA3 expression vector (Invitrogen), transfected into IEC-18 cells and stable transfectants were selected.

Determination of ILK, E-cadherin and $\beta_1$ integrin levels. The cellular levels of ILK and E-cadherin were determined by immunoblot using an affinity-purified polyclonal rabbit anti-ILK antibody 91-4, and an anti-E-cadherin antibody (Upstate Biotechnologies, Inc.). The cell surface expression of $\alpha_5 \beta_1$ integrins was estimated by immunoprecipitation of surface biotinylated cell lysates with a polyclonal rabbit anti-$\alpha_5 \beta_1$ antibody.

Immunofluorescent Staining. Fn matrix assembly was analyzed by immunofluorescent staining of cell monolayers (Wu et al. (1995) Cell 83:715-724). Cells were suspended in the α-MEM medium containing 5% FBS and other additives as specified in each experiment. Cells were plated in 12-well HTC.sup.R slides (Cel-Line, Inc., Newfield, N.J.; 50 μl/well) at a final density of $2 \times 10^5$ cells/ml and cultured in a 37° C. incubator under a 5% $CO_2$-95% air atmosphere. Cells were fixed with 3.7% paraformaldehyde, and staining with the polyclonal rabbit anti-Fn antibody MC54 (20 μg/ml) and Cy3-conjugated goat anti-rabbit IgG antibodies (Jackson ImmunoResearch Lab, Inc, West Grove, Pa.; 2.5 μg/ml). Stained cell monolayers were observed using a Nikon FXA epifluorescence microscope and representative fields were photographed using Kodak T-Max 400 or Ektachrome 1600 direct positive slide film. To obtain representative images, exposure times for different experimental conditions were fixed, using the positive, e.g., matrix forming cells, as the index exposure length.

In double staining experiments, 3.7% paraformaldehyde fixed cells were permeablized with 0.1% Triton X-100 in TBS containing 1 mg/ml BSA. The cells were then incubated with primary antibodies from different species as specified in each experiment. After rinsing, the bound primary antibodies were detected with species-specific Cy3- and FITC-conjugated secondary antibodies. Stained cell monolayers were observed using a Nikon FXA epifluorescence microscope equipped with Cy3 and FITC filters.

For inhibition studies, ILK13-A4a cells that overexpress ILK were plated in 12-well HTC.sup.R slides in the α-MEM medium containing 5% FBS and other additives as specified (2 μM anti-29 kDa Fn fragment antibody, 2 μM rabbit control IgG, or 4.2 μM of one of the following Fn fragments: 110 kDa RGD containing integrin binding fragment of Fn, 70 kDa aminoterminal fragment of Fn or 60 kDa gelatin binding fragment of Fn). The cells were cultured for four hours, and then fixed and stained with the polyclonal rabbit anti-Fn antibody and the Cy3-conjugated goat anti-rabbit IgG antibodies as described above.

Isolation and Biochemical Characterization of Extracellular Matrix Fn. To isolate and biochemically characterize extracellular matrix Fn, the cells were cultured in 100 mm tissue culture plates (Corning, Inc., Corning, N.Y.) in α-MEM medium supplemented with 5% FBS, 2 mM L-glutamine, 3.6 mg/ml glucose, 10 μg/ml insulin and other additives as specified in each experiment for two days. Then the cell monolayers were washed three times with PBS containing 1 mM AEBSF and harvested with a cell scraper. The extracellular matrix fraction was isolated by sequential extraction of the cells with (1) 3% Triton X-100 in PBS containing 1 mM AEBSF; (2) 100 μg/ml DNase I in 50 mM Tris, pH 7.4, 10 mM $MnCl_2$, 1 M NaCl, 1 mM AEBSF and (3) 2% deoxycholate in Tris, pH 8.8, 1 mM AEBSF (Wu et al., supra.) Fn in the deoxycholate insoluble extracellular matrix fraction was analyzed by immunoblot with polyclonal rabbit anti-Fn antibody MC54 and an ECL detection kit as previously described (Wu et al. (1995) J. Cell Sci. 108:821-829).

Colony formation in soft agar. ILK13-A1a3 cells that overexpress ILK ($3 \times 10^5$/well), and Ras-37 cells that overexpress H-RasVal12 ($2 \times 10^3$/well) were plated in 35 mm wells, in 0.3% agarose and assayed for colony growth after three weeks as described above. Fn fragments were incorporated in the agar at the final concentrations indicated.

Tumor formation in athymic nude mice. IEC-18, ILK14, or ILK13 cells were resuspended in PBS and inoculated subcutaneously into athymic nude mice ($10.sup.7$/mouse). Six mice were inoculated per cell line. In situ tumor formation was assessed after 3 weeks.

Tyrosine Phosphorylation of p125.sup.FAK in ILK cells. ILK13-A1a3 and ILK14-A2C3 cells growing in monolayer culture were harvested using 5 mM EDTA/PBS (Phosphate Buffered Saline, pH 7.6) and the cells were washed twice in PBS. Cells were resuspended in serum free medium and then transferred to plain tissue culture plates (Nunc), tissue culture plates precoated with 10 μg/ml Fn (Gibco/BRL) or maintained in suspension. For the suspension control cells were kept in 50 ml rocker tube. After 1 hour incubation at 37° C. in 5% $CO_2$ cell monolayer (for the adherent controls) and cell pellet (for the suspension controls) were washed twice in ice-cold PBS and lysed in NP-40 lysis buffer (1% NP-40; 150 mM NaCl; 50 mM Tris, pH 7.4; 1 mM EDTA, 1 mM PMSF, 0.2 U/ml aprotinin, 2 μg/ml leupeptin and 1 mM Sodium Vanadate). FAK was immunoprecipitated from 400-500 μg of total cell extract using 4 μg mouse monoclonal anti-p125.sup.FAK antibody and Protein A-Agarose conjugate (UBI). Immune complexes were washed three times in lysis buffer, boiled in SDS-PAGE sample buffer and run on a 7.5% gel. Resolved proteins were transferred to Immobilon-P (Millipore) and membrane blocked in 5% BSA (Sigma) in TBST (0.1% Tween-20 in Tris Buffered Saline, pH 7.4). Tyrosine-phosphorylated FAK was detected using the RC20H recombinant antibody (HRP-conjugate, Transduction) and ECL detection system (Amersham).

Results

Stimulation of Fn matrix assembly by ILK, To determine whether ILK plays a role in regulation of Fn matrix assembly, the ability of cells expressing different levels of ILK to assemble a Fn matrix was analyzed. IEC-18 rat intestinal epithelial cells assembled a small amount of Fn matrix consisting of mostly short fibrils. ILK13-A1a3 cells, which were isolated from the IEC-18 cells stably transfected with a pRC/CMV expression vector containing full length ILK coding sequence, express a much higher level of ILK than the parental IEC-18 cells. The ILK overexpressing ILK13-A1a3 cells assembled an extensive Fn matrix resembling that formed by fibroblasts, whereas control transfectants (ILK14-A2C3), which express a similar level of ILK as the parental IEC-18 cells, assembled a small amount of Fn matrix that is indistinguishable from that of the IEC-18 cells fibroblasts. To exclude the possibility that the observed effect depends on a specific clone, ten additional cell lines were analyzed that were independently isolated from the cells transfected with the pRC/CMV-ILK expression vector (ILK13-A4a, A1d11, A4c, A4c3 and A41) or the control vector (ILK14-A2C6, A2a3, A2g3, A2g8 and A3a1) Fn matrix assembly was dramatically increased in all six ILK-overexpressing cell lines (Table 3). On the other hand, all six control cell lines assembled a low level of Fn matrix resembling that of the parental IEC-18 cells. In marked contrast to overexpression of ILK, overexpression of an oncogenic H-Ras mutant in which the twelfth amino acid residue is mutated (H-RasVal12) in the IEC-18 cells abolished the assembly of Fn fibrils.

TABLE 3

Fn matrix assembly by cells expressing different levels of ILK

| Cell Line | ILK Expression level | Extracellular Fn matrix level |
|---|---|---|
| ILK13 (A1a3, A4a, A1d11, A4c | High (wild type ILK) | High |
| ILK14 (A2C6, A2C3, A2a3, A2g3, A2g8 and A3a1), IEC-18, MT-ILK6 (E2) | Low (wild type ILK) | Low |
| GH31RH | High (kinase-inactive mutant) | Low |

The ILK 13 cell lines were independently isolated from IEC-18 rat intestinal epithelial cells that were stably transfected with a pRC/CMV expression vector containing full length ILK coding sequence and they express a much higher level of ILK than the parental IEC-18 cells. The ILK 14 cells were control transfectants (41). The MT-ILK1 (IIB8) cells were isolated from IEC-18 cells transfected with the sense ILK expression vector (MT-ILK1). The MT-ILK6 (E2) cells were isolated from IEC-18 cells transfected with the anti-sense ILK expression vector (MT-ILK6). The GH31R cells were isolated from IEC-18 cells transfected with a pcDNA3 expression vector encoding a ILK kinase-inactive mutant in which glutamic acid residue 359 was replaced with a lysine residue. The relative ILK expression levels were based on immunoblot analysis with anti-ILK antibodies.

To further confirm a regulatory role of ILK in Fn matrix assembly, IEC-18 cells were transfected with expression vectors containing full length ILK cDNA in the forward (sense) or the reverse (anti-sense) orientation that were under the control of metallothionein promoter (MT). The MT-ILK1 (IIB8) cells, which were derived from the IEC-18 cells transfected with the sense ILK expression vector, expressed more ILK than the MT-ILK6 (E2) cells that were derived from the IEC-18 cells transfected with the anti-sense ILK expression vector. The difference in ILK expression was maximized when the cells were grown in the presence of $Zn^{++}$ and $Cd^{++}$ Consistent with a critical role of ILK in Fn matrix assembly, the ILK overexpressing MT-ILK1 (IIB8) cells exhibit a much high Fn matrix assembly than the MT-ILK6 (E2) cells that have a much lower level of ILK. Thus, overexpression of ILK, either driven by a CMV promoter or driven by a metallothionein promoter, stimulates Fn matrix assembly.

Involvement of integrin-linked kinase activity in the cellular regulation of Fn matrix assembly. To test whether the kinase activity is involved in the stimulation of Fn matrix assembly by ILK, a kinase-inactive ILK mutant (GH31R) was overexpressed in the IEC-18 cells. Unlike cells overexpressing the wild type ILK, cells overexpressing the kinase-inactive ILK mutant did not assemble an increased amount of Fn into the extracellular matrix. Thus, the kinase activity is critical in the cellular signal transduction leading to the up-regulation of Fn matrix assembly.

Biochemical characterization of Fn matrix assembled by cells overexpressing ILK. The Fn matrix deposited by fibroblastic cells is characterized by insolubility in sodium deoxycholate. To determine whether Fn matrix induced by overexpression of ILK in the epithelial cells shares this characteristic, the cell layers were extracted with 2% sodium deoxycholate and the insoluble matrix fractions analyzed by immunoblotting. The cells overexpressing ILK (A1a3, A4a and IIB8) assembled much more Fn into the deoxycholate insoluble matrix than the cells that express relatively low level of ILK (A2C6, A2C3, and E2). By contrast, cells overexpressing H-RasVal12 failed to deposit detectable amount of Fn into the detergent insoluble matrix (H-Ras). These results are consistent with the immunofluorescent staining data. Taken together, they provide strong evidence supporting an important role of ILK in regulation of Fn matrix assembly.

Participation of the RGD containing integrin-binding domain and the amino terminal domain of Fn in ILK stimulated Fn matrix assembly. Integrin-mediated Fn matrix assembly requires at least two discrete portions of Fn, the RGD containing integrin-binding domain and the aminoterminal domain. To determine whether these domains also participate in Fn matrix assembly induced by overexpression of ILK, the 110 kDa RGD containing fragment, the 70 kDa aminoterminal domain of Fn, and an antibody against the amino terminal domain of Fn (anti-29 kDa) were utilized. Both the antibody and the Fn fragments decreased the Fn fibril formation induced by ILK. The inhibition was specific, as neither irrelevant rabbit IgG nor a 60 kDa Fn Fragment lacking the amino terminus inhibited the Fn matrix assembly. Thus, both the RGD containing integrin-binding domain and the amino terminal domain of Fn are involved in Fn matrix assembly promoted by overexpression of ILK, suggesting a role of Fn-binding integrins in this process.

Co-distribution of $\alpha_5 \beta_1$ integrin and Fn matrix in cells overexpressing ILK. To begin to identify which Fn-binding integrin mediates Fn matrix assembly induced by overexpression of ILK, cells overexpressing ILK were stained with a hamster monoclonal anti-rat α5 integrin antibody and a rabbit polyclonal anti-Fn antibody. The double-staining experiments showed that $\alpha_5 \beta_1$ integrin was co-localized with Fn fibrils in A1a3 cells that overexpress ILK. In contrast, staining of the cells with an anti-rat $\beta_3$ integrin antibody revealed no distinctive staining. These results suggest that $\alpha_5 \beta_1$ integrin, but not $\beta_3$ integrins, participate in the Fn matrix assembly induced by overexpression of ILK.

In contrast to cells that overexpress ILK, cells expressing a lower level of ILK (A2C6) have fewer clusters of $\alpha_5 \beta_1$ integrin that could be detected by immunofluorescent staining, although these cells express the same level of cell surface $\alpha_5 \beta 1$ integrin as the cells overexpressing ILK. Moreover, in marked contrast to A1a3 cells that overexpress ILK, many of the structures containing $\alpha_5 \beta_1$ integrin in the A2C6 cells lacked detectable Fn, indicating that overexpression of ILK enhances the binding of Fn to $\alpha_5 \beta_1$ integrin.

Effect of ILK overexpression on the formation of focal adhesion and matrix contacts. Cell adhesion to extracellular substrates is mediated by transmembrane complexes termed focal adhesions which contain integrin, vinculin, and other cytoskeletal proteins. A connection between extracellular Fn and the intracellular actin cytoskeleton involving the integrin β cytoplasmic domain is required for the assembly of Fn fibrils. A2C3 cells that express low levels of ILK formed abundant focal adhesions visualized by staining with an anti-vinculin antibody. However, only a small amount of $\alpha_5 \beta_1$ integrin and Fn were co-localized with the focal adhesions in A2C3 cells.

Overexpression of ILK promoted co-localization of $\alpha_5 \beta_1$ integrin and Fn with vinculin. Thus, while cells expressing a relatively low level of ILK are not defective in the assembly of focal adhesion, a higher level of ILK promotes the assembly of complexes containing vinculin, $\alpha_5 \beta_1$ integrin and Fn matrix. Overexpression of ILK down-regulates E-cadherin. E-cadherin is an important epithelial cell adhesion molecule mediating cell-cell interactions. Because overexpressing ILK in epithelial cells disrupted the characteristic "cobble-stone" epithelial morphology of the epithelial cells, the effect of ILK expression on the cellular level of E-cadherin was studied. The level of E-cadherin in cells expressing different amount of ILK was determined by immunoblot using an anti-E-cadherin antibody. The parental IEC-18 epithelial cells expressed abundant E-cadherin. Overexpression of H-RasVal12 in IEC-18 cells reduced the level of E-cadherin. Strikingly, E-cadherin was completely eliminated in ILK13-A1a3 and A4a cells that overexpress ILK, whereas it was present at a normal level in ILK14-A2C3 and A2C6 cells that express a similar level of ILK to the parental IEC-18 cells. These results indicate an inverse correlation between the level of ILK and that of E-cadherin.

In contrast to E-cadherin level, overexpression of ILK did not alter the ability of the cells to phosphorylate focal adhesion kinase (pp125.sup.FAK) in response to cell adhesion to Fn, indicating that tyrosine phosphorylation of pp125.sup.FAK does not transduce the signals leading to the alterations observed upon ILK overexpression, and in particular tyrosine phosphorylation of pp125.sup.FAK does not play a regulatory role in ILK induced Fn matrix assembly.

Induction of in vivo tumorigenesis by overexpression of ILK. To assess a potential role of ILK in tumorigenesis, cells expressing varying levels of ILK were injected into athymic nude mice subcutaneously. Tumors arose within three weeks in 50% to 100% of the mice injected with the ILK13 cells (10.sup.7 cells/mouse) that overexpress ILK, whereas no tumors were detected in the mice that were injected with the same number of the IEC-18 or ILK14 cells expressing lower levels of ILK (Table 4). Thus, overexpression of ILK in these epithelial cells promotes tumor formation in vivo.

TABLE 4

Tumorigenicity of ILK overexpressing IEC-18 Cells

| Cell Line | Number of Mice with Tumors at 3 weeks |
| --- | --- |
| IEC-18 | 0/6 |
| ILK14-A2C3 | 0/6 |
| ILK13-A1a3 | 6/6 |
| ILK13-A4a | 3/6 |

Athymic nude mice were inoculated subcutaneously with the cells expressing high (ILK13-A1a3 and A4a) or low (IEC-18 and ILK14-A2C3) levels of ILK ($10^7$ cells/mouse in PBS). The mice were monitored for tumor formation at the site of inoculation after three weeks.

Inhibition of ILK induced cell growth in soft agar by amino terminal fragments of Fn that inhibit matrix assembly. One of the hallmarks of tumor forming cells is that their growth is less dependent on anchorage as measured by their ability to grow in soft agar culture. Similar to cells overexpressing H-Ras, cells overexpressing ILK were able to grow in soft agar. However, in marked contrast to the H-Ras overexpressing cells, ILK overexpressing cells assembled an abundant Fn matrix (Table 3). It was therefore tested whether the ability of the ILK overexpressing cells to grow in soft agar culture is related to the elevated level of Fn matrix assembly. The cells overexpressing ILK and the cells overexpressing H-Ras, respectively, were cultured in soft agar either in the presence or absence of the 70 kDa Fn amino terminal fragment, which inhibits the ILK induced Fn matrix assembly. The 70 kDa Fn fragment significantly inhibited the ILK induced "anchorage independent" growth in soft agar. Similar inhibition was observed with the 29 kDa fragment of Fn. In contrast, the H-Ras induced anchorage independent growth in soft agar was not inhibited by the 70 kDa Fn fragmen. Moreover, the ILK induced cell growth in soft agar was not inhibited by the 60 kDa Fn Fragment which does not inhibit the Fn matrix assembly induced by ILK. These results suggest that the cell growth in soft agar induced by ILK, but not that induced by H-Ras, is at least partially mediated by a Fn matrix.

Discussion

The overexpression of ILK results in a loss of E-cadherin protein expression, offering a possible explanation for the loss of cell-cell contact in these cells. Indeed, losses of cell-cell adhesion have been implicated in tumorigenicity in vivo. ILK overexpressing cells are tumorigenic in nude mice in contrast to the parental IEC-18 intestinal epithelial cells and the control transfected clones. Thus, ILK can be considered to be a proto-oncogene. Another important finding is the apparent involvement of ILK in Fn matrix assembly. Overexpression of ILK in IEC-18 cells stimulated Fn matrix assembly. This is a property of transfected cell clones constitutively overexpressing ILK, and also of transfected clones in which ILK expression is induced using a metallothionein inducible promoter. Furthermore, Fn matrix assembly is impaired when an anti-sense ILK cDNA is induced resulting in decreased ILK expression.

The ILK-stimulated Fn matrix assembly was inhibited by the amino-terminal domain of Fn, as well as the RGD-containing integrin binding domain of Fn, suggesting that RGD-binding integrins mediate ILK functions in. Fn matrix assembly. Due to the unavailability of anti-integrin function blocking antibodies against rat integrins, it has not been possible to identify directly the specific integrin(s) involved in the enhanced Fn binding and matrix assembly. However, using immunofluorescence analysis, the $\alpha_5 \beta_1$ integrin, but not $\alpha.sub.v \beta_3$, was co-localized with Fn fibrils in the ILK overexpressing cells, implicating $\alpha_5 \beta_1$ in the matrix assembly process. Furthermore, ILK overexpression promoted the co-localization of Fn with $\alpha_5 \beta_1$ and vinculin, whereas in the parental IEC-18 cells and control transfected cells vinculin containing focal adhesion plaques were not co-localized with Fn.

The kinase activity of ILK is clearly important in the stimulation of Fn matrix assembly, as overexpression of a kinase-inactive ILK mutant failed to enhance Fn matrix assembly. However, because ILK has potential binding sites for integrins and probably other intracellular signaling molecules, and because Fn matrix assembly can be regulated by post ligand occupancy events, it is possible that other activities of ILK may also play important roles in the stimulation of Fn matrix assembly.

Although ILK overexpressing IEC-18 cells express same levels of integrins as the parental cells, the ILK overexpressing cells gain the ability to grow in an anchorage independent manner in soft agar, and are tumorigenic in nude mice, and they organize a prolific Fn matrix. The same IEC-18 cells transfected with an activated form of H-ras, do not assemble a Fn matrix, but nevertheless are highly tumorigenic in nude mice. This represents a novel pathway of oncogenic transformation which is distinctive from H-Ras induced transformation and involves ILK and enhanced Fn matrix assembly. In fact, the ability to form a Fn matrix is important for the anchorage independent growth of transforming growth factor β (TGF β) treated fibroblasts. Fn matrix assembly also seems to be important for anchorage-independent growth in soft agar of the ILK overexpressing cells since inhibition of matrix assembly by the 29 kDa and 70 kDa amino terminal fragments of Fn, results in an inhibition in colony formation in soft agar.

The expression of activated p21.sup.ras results in the disregulation of multiple signaling pathways and typically renders cells serum-independent, as well as anchorage independent for cell growth. On the other hand, the overexpression of ILK does not result in serum-independent cell growth, but induces anchorage-independent cell growth. These results indicate that ILK normally regulates adhesion-dependent signaling pathways and that the disregulation of ILK (e.g. by overexpression) induces anchorage-independent cell growth specifically. It is likely that ILK mediated signaling may be involved in the regulation of integrin inside-out signaling, as activated integrins are required for Fn matrix assembly.

The ability to assemble an extensive Fn fibrillar matrix is a property of mesenchymal cells and it is intriguing that the stimulation of this activity by ILK overexpression in the epithelial cells is accompanied by a dramatic downregulation of cellular E-cadherin expression. Numerous previous studies have established that cellular E-cadherin level or activity is downregulated during epithelial-mesenchymal transition. Moreover, in a recent study, Zuk and Hay demonstrated that inhibition of $\alpha_5$ 1 integrin, which is a substrate of ILK, significantly inhibited epithelial-mesenchymal transition of lens epithelium. It is now also widely accepted that many invasive carcinomas exhibit a loss of E-cadherin expression, and E-cadherin gene has been found to be a tumor/invasion-suppressor gene in human lobular breast cancer. The tumor suppressor gene fat in *Drosophila* is also homologous to cadherins. ILK may therefore be involved in coordinating cell-matrix adhesion and cell-cell adhesion in epithelial-mesenchymal transition, and overexpression of ILK may drive epithelial cells towards a mesenchymal phenotype and oncogenic transformation.

The ILK stimulated Fn matrix assembly may allow enhanced interaction of Fn with $\alpha_5 \beta_1$. This integrin has recently been shown to be specific in supporting survival of cells on Fn, although no direct correlation was found between Fn matrix assembly and $\alpha_5 \beta_1$ mediated cell survival. This latter conclusion was derived from the use of wild type $\alpha_5 \beta_1$ and $\alpha_5$ cytoplasmic deleted ($\alpha_5$ .DELTA.C$\beta_1$) mutants. It is likely that for cell survival, both receptor interaction with Fn, as well as proper intracellular interactions are required. ILK overexpression in IEC-18 cells induces cell survival in suspension cultures largely due to the up-regulation of expression of cyclin $D_1$ and cyclin A proteins:

EXAMPLE 12

Expression of ILK in Human Colon Carcinoma Cells

Tumor (T) or adjacent normal (N) tissue from patients biopsied for colon carcinoma were analyzed for the expression of ILK or LEF-1 by Western blot analysis. ILK activity was further determined by an in vitro kinase assay, as described in previous examples.

These data demonstrate the strong expression of ILK in colon carcinomas, indicating an association with transformation. In accordance with the data presented in the previous example, LEF-1 expression is closely tied to ILK expression.

EXAMPLE 13

Phosphoinositide-3-OH Kinase-Dependent Regulation of GSK-3 and PKB/AKT by ILK

The amino acid sequence of ILK contains a sequence motif found in pleckstrin homology (PH) domains (Klarulund et al. (1997) Science 275:1927-1930). This motif has been shown to be involved in the binding of phosphatidylinositol phosphates (Lemmon et al. (1996) Cell 85:621-624). Amino acids critical to the binding of such lipids to the PH domain are completely conserved in ILK. The phosphatidylinosital 3,4,5, triphosphate binding sites are the lysines at positions 162 and 209 (SEQ ID NO:2). The PH motifs are comprised of residues 158-165 and 208-212 (SEQ ID NO:2). There is a high degree of sequence identity within this motif between ILK and other PH-domain containing proteins such as cytohesin-1 (a β2 integrin cytoplasmic domain interacting protein) and GRP-1. It was determined that ILK activity is influenced by the presence of phosphatidylinosital-3,4,5, triphosphate, and interacts with other kinase proteins in this pathway.

Materials and Methods

Stable-Transfected Cells. IEC-18 rat epithelial transformed cells are grown in Alpha-ME Media with 5% Fetal Calf Serum (GIBCO-BRL), insulin, glucose and L-glutamine. All cells are grown in the absence of antibiotics and anti-fungal agents. They are harvested and lysed at 80% confluency, with the Lysis Buffer used in the following Kinase Assays. The lysates are quantified with the Bradford Assay.

Transient Transfection. On the day before transfection, the 293 Human Embryonic Kidney cells are split such that there will be approximately 1 to 1.2 million cells (68% confluent) in a 100 mm (Falcon) dish at the time of transfection. The cells are fed with DME Media and 10% Donor Calf Serum (GIBCO-BRL). The cells are grown in the absence of antibiotics and anti-fungal agents. The use of poly-L-lysine is optional.

Precipitate plasmids using the calcium/phosphate method with 40 μg of DNA per dish (15 to 20 μg of plasmids containing ILK construct; 7 to 10 μg of plasmids containing GSK-3B construct; use empty vectors when appropriate), and a 2×HEPES-buffered saline (HeBS) solution of ph 7.05. Allow precipitates to transfect overnight in 3% carbon dioxide environment, in 7 ml of DME Media and 5% donor calf serum. The next morning, remove the precipitate and medium mixture. Then continue to propagate the cells with 10 ml of DME media and 10% donor calf serum until the time of harvest. If the cell become too confluent, they can be split. Harvest the cell lysates 48 to 60 hours after transfection.

GSK-3B Kinase Assay. Lyse the cells directly from the dish and collect the cytoplasmic lysate [Lysis Buffer: 150 mM NaCl, 1% NP-40, 0.5% DOC, 50 mM ph 7.5 Hepes, 1 μg/ml Leupeptin, 1 μg/ml Aprotinin, 1 mm PMSF and 0.1 mM Sodium orthovanadate]. Incubate overnight, 300 μg of precleared cell protein with 1 μl of GSK-3B antibody (Alphonse antibody from James Woodgett) in a 500 μl volume. Capture the immunocomplex by incubating 25 to 30 μl of protein A-sepharose beads with the lysate for 2 hours at 4 degrees centigrade. Collect the beads and wash with cold Lysis Buffer and Kinase Last Wash Buffer, [10 mM Magnesium Chloride, 10 mM Manganese Chloride, 50 mM ph 7.0 Hepes, 0.1 mM Sodium Ortho-Vanadate and 1 mM DTT]. Remove all traces of the supernatant and add 25 μl of Kinase Reaction Buffer [50 mM ph 7.0 Hepes, 10 mm Manganese Chloride, 10 mM Magnesium Chloride, 2 mM Sodium Fluoride, 1 mM Sodium orthovanadate, 1 μl of Glycogen Syntase-1 peptide (from James Woodgett)/reaction and 5 μCi/reaction of ATP(gamma 32 phosphate)] to the beads. Incubate the mixture for 25 minutes at 30° C. and stop the reaction with the addition of 30 μl of 2× reducing sample buffer. Incubate the mixture at 40 for 10 minutes. Do not boil the samples. Run the samples on a Tricine Gel (Schlaeggen and von Jaggow 1987 Anal Biochem 166:368-79) with 15 teeth, 1.5 mm Hoefer comb and apparatus overnight at a constant voltage of 110 Volts. Visualize the wet gel with a phosphorimager or via autoradiography.

ILK Kinase Assay. This technique is similar to the GSK-3B Kinase assay. The only differences are the following. For the formation of the immunocomplex, 1.5-2 μg of antibody is required per sample (200 to 300 μg of protein in a 500 to 600 μl volume). The composition of the Kinase Reaction Buffer contains 5 μg of myelin basic protein per reaction instead of the GSK-1 peptide. The reaction is stopped by the addition of 30 μl of 2× non-reducing sample buffer, followed by 3 min boiling of the samples. The samples are separated on a 15% SDS-polyacrylamide gel. The fixed and dried gel is visualized via autoradiography or phosphorimagery.

Kinase Activation Assessment of Transient Transfected 293 HEK Cells. 48 hours after transfection with the various constructs, 293 HEK cells are serum starved, because the cells must be quiescent prior to being activated by growth factors. The cultures are washed 3× with serum-free DMEM and incubated for 12 hrs in serum-free DMEM.

For activating the cell, the serum-free media is removed and the cultures are incubated with DMEM (4 ml per 100 mm dish) supplemented with the appropriate concentration of growth factors (100 nM Insulin or 5 nM IGF-1), and in the presence or absence of a P13 Kinase inhibitor (50 μM LY294002). The activation times vary.

The activation is stopped by washing the cultures 3× with cold PBS, followed by lysing the cells on the dishes with NP40-DOC lysis buffer. Allow the lysis buffer to work for 30 minutes on ice, before harvesting. Spin the whole cell lysates at 15000 rpms for 15 min and collect the supernatant. Quantify the supernatant (cytoplasmic lysate) with the Bradford Assay. The lysates are now ready to be used for immunoprecipitation or mixed with 4× sample buffer for Western Blot Analysis.

Assessment of ILK activation by insulin on IEC-18 cells. IEC 18 cells are rat colon epithelial cells that are cultured routinely in α-MEM medium supplemented with insulin (10 mg/liter), glucose 3.6 g/liter, and 5% FCS. When IEC 18 cells are grown to 80% confluence, they are serum starved for 18 hours prior to activation by insulin. Before addition of insulin, media are removed and 4 ml of α-MEM+insulin 6 μM is added to the 100 mm dishes. PI3 kinase inhibitors such as LY294002 at 50 μM or wortmannin at 200 nM are added optionally to block P13 kinase dependent ILK activation. At the designated times, dishes are washed 3× with ice cold PBS and cells are lysed in 500 μl lysis buffer: 150 mM NaCl, 1% NP40, 0.5% sodium deoxycholate, 50 mM Hepes pH 7.5, 10 μg/ml leupeptin, 1 mM PMSF, 2.5 μl aprotinin/ml lysis buffer, NaF 5 mM, Sodium vanadate 1 mM. After assessment of protein concentration by Bradford assay, 500 μl samples containing 200 μg of proteins are incubated for 2 hrs at 4° C. with 20 μl of Protein A-Sepharose to preadsorb the non specific kinases. The lysate is then incubated overnight with 2 μg of rabbit anti ILK antiserum at 4° C. under rotation.

The immunocomplexes are then captured by incubating the lysate with 15 μl of Protein A Sepharose for 2 hrs at 4° C. The beads are washed 2× with lysis buffer. The beads are washed 2× with last wash buffer: 10 mM $MgCl_2$, 10 mM $MnCl_2$, 50 mM Hepes pH 7.0, 0.1 mM sodium orthovanadate, 2 mM NaF, 1 mM DTT. After aspirating completely the buffer, the beads are then mixed with 25 μl of kinase reaction mixture: 22.5 μl of kinase buffer (10 mM $MgCl_2$, 10 mM $MnCl_2$, 50 mM Hepes pH 7.0, 1 mM sodium orthovanadate, 2 mM NaF); 2 μl of myelin basic protein at 2 mg/ml (UBI, #13-104), 5 μCi of $^{32}P$ γ-ATP. The kinase reaction is allowed to proceed for 25 min at 30° C. The reaction is stopped by addition of 30 μl of 2× sample buffer and boiling for 3 min. The samples an then electrophoresed on a 12% SDS-PAGE gel. Phosphorylation level of MBP is assessed by phosphorimager analysis or exposure to an X ray film.

Assessment of ILK kinase activity in 3T3 cells stably transfected with active or inactive PI3 kinase. The cDNAs coding for the HA-tagged P110 subunit of the PI3 kinase in pcDNA3 were used. 3T3 cells were grown in DMEM with 10% donor calf serum in exponential conditions. The 3T3 cells were harvested by trypsinization and washed once with HeBs buffer: 20 mM Hepes pH 7.05, 137 mM NaCl, 5 mM KCl, 0.7 mM $Na_2HPO_4$, 6 mM glucose. $10.sup.7$ cells were then resuspended in 0.8 ml of ice-cold HeBs containing 20 μg of uncut DNA. Electroporation was performed with a Bio-Rad gene pulser set to 280 V, 9.60 pF. After electroporation, cells were allowed to sit on ice for 10 min before being diluted into 24 ml DMEM, 10% DCS and plated on a 150 mm dish. After 2 day recovery, selection was initiated by the addition of G418 at the final concentration of 0.8 mg/ml to the culture medium. After 2 weeks, the clones appeared and the transfectants were cloned by serial dilution and culture in 96 well microwell plates. Clones expressing the HA-tagged p110 subunit were expanded and used for ILK kinase assay in serum starved cells treated with or without with LY 294002.

Transfection of 293 cells protocol. 293 cells have to be exponentially grown for optimal transfection. Typically they are passaged every 3 days by splitting them 1/10. Medium is DMEM medium supplemented with 10% donor calf serum. $CaCl_2$ M solution: to 14.7 g of $CaCl_2$ $2H_2O$, add 50 ml of water to 50 ml. Filter sterilize through a 0.45 μm nitrocellulose filter. Store aliquots at −20° C. 2×HBS solution: to 16.4 g NaCl, add 11.9 g Hepes and 0.21 g $Na_2HPO_4$ and dissolve in 800 MI H2O. Adjust the pH to 7.12 and add water to 1000 ml. Filter sterilize through a 0.22 μM filter and store at −20° C. Plasmid solution: 15 μg of ethanol precipitated plasmids are used per transfection. They are resuspended in sterile $H_2O$ and mixed with 62 μl $CaCl_2$ 2M solution. $H_2O$ is added to 500 μl final.

Plate $1×10^6$ 293 cells per 100 mm dish in 10 ml medium 24 h prior to transfection. Mix 50 μl of plasmid solution to 500 μl of 2×HBS solution dropwise at the same time as bubbling the combined mixture with a Pasteur pipette connected to a pipetman. Vortex the mixture for 1 min. and let it stand for 20 min. Add dropwise the 1 ml mixture to the cells and grow them in 3% $CO_2$ atmosphere. After 16 hrs of culture, change the media and grow the cells in normal 5% $CO_2$ atmosphere. After 48-60 hrs, the cells are harvested for the assay.

Assessment of AKT Phosphorylation by ILK in 293 Cells.

Kinase assay. After cotransfection of 293 cells with HA-AKT and ILK, wild type or kinase dead, the cells are serum starved for 12 hours and submitted for activation by growth factors for designated times. Cells are then lysed with 500 μl lysis buffer: 50 mM Tris-HCl pH 7.4, 0.5% NP40, 1 mM EDTA, 1 mM EGTA, 50 mM NaF, 10 mM 5-glycerophosphate, 0.25 mM sodium vanadate, 1 μM microcystin LR, PMSF 1 mM, aprotinin 2.5 μl/ml, leupeptin 10 μg/ml. Prepare a 1:1 slurry of protein G-anti HA mouse Mab beads as follows: Wash the proteinG-sepharose beads with solubilization buffer 3×. Add 2 μg of anti HA antibody per assay point. Rotate at 4° C. for 1 hr. Wash with solubilization buffer 3×. Resuspend to 1:1 with solubilization buffer and add 40 μl to the lysates. Rotate the lysates with the beads for 1-2 hrs. Wash beads 3× with solubilization buffer containing 500 mM NaCl. Wash beads 2× with kinase buffer: 20 mM HEPES pH 7.4 25 mM β-glycerophosphate, 1 mM sodium vanadate, 1 mM DTT, 1 mM $MgCl_2$, 1 μM microcystin LR, PMSF and leupeptin.

Aspirate the beads completely. Add 20 μl kinase buffer containing 60 μM Crosstide (From UBI catalog #12-331). Keep cold until ready for kinase assay. Add 10 μl ATP solution (200 μM cold ATP and 10 μCi/sample $^{32}P$ γ-ATP in kinase buffer), vortex gently and place tubes in 30° C. water bath. At 15 min, spot 2 μl onto p81 chromatography paper, let dry for about 2 min, and immerse into 1% phosphoric acid. Wash blots 6-10× with 1% phosphoric acid and count in scintillation counter.

Western blot analysis of AKT (Ser473) phosphorylation state. After cell activation and lysis, the lysates are mixed with 4× sample buffer and heated to 95-100° C. for 5 minutes and cooled on ice. 20 μl of samples are run onto SDS-PAGE gels. Proteins are electotransfered on a PVDF membrane. Incubate membrane in 100 ml blocking buffer, i.e. TBS (Tris buffered saline) pH. 7.6 supplemented with 5% milk for 1-3 hrs. Incubate membrane and rabbit anti p-$^{473}S$ AKT antiserum (New England Bio Labs Cat No #9270) at the 1:1000 dilution in 10 ml primary antibody dilution buffer with gentle agitation overnight at 4° C.

Primary antibody dilution buffer: 1×TBS, 0.1% Tween 20 with 5% BSA. Wash 3 times for 5 minutes each with 15 m TBST. Incubate membrane with horse radish peroxidase (HRP)-conjugated secondary antibody (1:20,000) with gentle agitation for 1 hr at room temperature. Wash membrane 3 times for 5 minutes each with 15 m TBST. Incubate membrane with ECL reagent (Amersham) for 1 min at room temperature. Drain membrane of excess developing solution, wrap in Saran wrap and expose to X-ray film.

Assessment of regulation of ILK kinase by phosphoinositides. PtdIns(3)P, Ptdins(3,4)$P_2$ and PtdIns(3,4,5)$P_3$ were dried under nitrogen and resuspended at 0.1 mM in Hepes 10 mM, pH 7.0 with phosphatidylserine and phosphatidylcholine, both at 1 mM. The lipid suspensions were vortexed and further sonicated for 20 min in order to generate unilamellar vesicles. 11 μl of ILK5-GST in kinase buffer were combined to 4 μl of lipids and 25 μl of kinase reaction solution containing 2.5 μl of MBP and 5 μCi of $γ^{32}$ P-ATP. The reaction proceeded for 30 or 2 hrs at 30° C. The reaction was stopped by adding an equal volume of 2× sample buffer. The samples were run on a 12% non reducing SDS-PAGE gel.

Results

ILK activity is stimulated in vitro by phosphatidylinositol (3,4,5) trisphosphate (Ptdlns(3,4,5)P3) but not by phosphatidylinositol(3,4) bisphosphate (Ptdlns(3,4)P2), or phosphatidylinositol(3) monophosphate (Ptdins(3)P).

Since Ptdlns(3,4,5,)P3 is specifically generated upon receptor-mediated stimulation of PI(3)Kinase activity, it was determined whether ILK activity is stimulated in a PI(3)K dependent manner. PI(3)K is activated in response to a very wide range of extracellular stimuli, which include growth factors and cytokines, as well as by cell adhesion to ECM. The Ptdlns(3,4,5)P3 product of PI(3)K is a second messenger that acts on pathways that control cell proliferation, cell survival, and metabolic changes often through the activation of P70 ribosomal S6 Kinase (p70.sup.S6k) and protein kinase B (PKB), also known as AKT. PKB/AKT is a protooncogene and has been shown to be activated in a PI(3)K-dependent manner in response to growth factors, cytokines and cell-ECM interactions.

To determine whether ILK is activated in a PI(3)K-dependent manner, quiescent, serum-starved, IEC-18 intestinal epithelial cells were treated with insulin, which is known to activate PI(3)K. ILK activity is rapidly stimulated by insulin and this activation is inhibited by prior treatment of the cells with Wortmannin (200 nM), a specific inhibitor of PI(3)K. Another inhibitor, Ly294002, also inhibits this activation. ILK activity is rapidly stimulated upon plating cells on fibronectin. This activation is also PI(3)Kinase-dependent, since it is inhibited by LY294002. These data demonstrate that ILK activity is stimulated by growth factors, such as insulin, and also by cell-ECM interactions, in a PI(3)K dependent manner, most probably resulting from the direct interaction of PI(3)K generated Ptdlns(3,4,5)P3 with ILK.

To further demonstrate the role of PI(3)K in ILK activation, NIH3T3 cells were stably transfected with either constitutively activated P110 subunit of PI(3)K, or a kinase-dead mutant of PI(3)K, and ILK activity was determined in the transfected clones. ILK activity is several-fold higher in cells expressing constitutively active P110 subunit of PI(3)K, compared to control cells, or those expressing kinase-dead PI(3)K. Furthermore, the stimulated ILK activity in these cells is inhibited by prior incubation with Ly294002.

Since ILK overexpression in epithelial cells results in the translocation of β-catenin to the nucleus, it was determined whether the activity of GSK-3, a kinase that normally phosphorylates β-catenin, is regulated by ILK. GSK-3 activity is inhibited when cells encounter Wnt, a matrix associated protein involved in cell fate determination. The inactivation of GSK-3 results in the inhibition of phosphorylation of □-catenin and its subsequent stabilization and nuclear accumulation. ILK may also contribute to the nuclear localization of β-catenin by inhibiting GSK-3 activity.

Although GSK-3 is expressed in all IEC-18 cell transfectants, its activity is dramatically inhibited in the ILK overexpressing ILK-13 cells, but not in IEC-18 cells stably expressing a kinase-dead ILK. As expected, ILK activity is about 5-fold higher in ILK-13 cells compared to the control cells. To determine whether this inhibition of GSK activity is due to ILK, transient transfection assays were carried out in 293 human embryonal kidney epithelial cells. Co-transfection of HA-tagged-GSK-3 together with wild type ILK results in profound inhibition of GSK-3 activity, demonstrating that kinase active ILK can inhibit GSK-3 activity. Co-transfection with kinase-dead ILK did not result in GSK-3 inhibition, but reproducibly resulted in increased GSK-3 activity over basal levels. These results suggest that the kinase-dead ILK may be acting in a dominant-negative manner by suppressing the function of transfected and endogenous ILK.

Since GSK-3 activity can also be regulated by PKB/AKT in a PI(3)K-dependent manner, and since it has previously been shown by others that integrin engagement stimulates PI(3)K activity leading to the activation of PKB/AKT, it was determined whether ILK might be upstream of PKB and may regulate its phosphorylation and activation. Co-transfection in 293 cells of HA-tagged PKB with wild-type ILK results in specific phosphorylation of PKB on serine-473, with the concomitant activation of its activity. Furthermore, co-transfection with kinase-dead ILK results in a distinct inhibition of serine-473 phosphorylation, demonstrating again that this form of ILK may be competing with endogenous ILK and thus behaving in a dominant-negative manner in the regulation of phosphorylation and activation of PKB. The identification of the protein kinases involved in the PI(3)K-mediated activation of PKB has been the subject of intense study, and has been extensively reviewed recently (Downward (1997) Science 279:673-674). Ptdlns(3,4,5)P3 can bind to the PH domain of PKB resulting in its targeting to the plasma membrane and exposure of threonine-308. A constitutively active kinase, PDK-1, then phosphorylates PKB on threonine-308. However, this phosphorylation alone is not sufficient to fully activate PKB, which also needs to be phosphorylated on serine-473 by an as yet unidentified kinase (PDK-2), in a Ptdins(3,4,5)P3-dependent manner. The present data shows that ILK, which is activated by Ptdlns(3,4,5)P3, can phosphorylate PKB on serine-473, resulting in its full activation, thus demonstrating that ILK is directly upstream of PKB in the transduction of PI(3)K-dependent signals to PKB.

In summary, the activity of ILK can be stimulated by Ptdlns(3,4,5)P3 in a PI(3)K-dependent manner and that it can then phosphorylate PKB on serine-473, resulting in its activation. ILK also inactivates GSK-3 activity. This inhibition may be indirect, occurring via PKB/AKT, as this kinase can phosphorylate GSK-3 on serine-9, but it is possible that ILK can also directly phosphorylate GSK-3 and inactivate it, independently of PKB. It will be interesting to determine whether, like ILK, PKB activation also results in the nuclear translocation of β-catenin and activation of Lef-1/β-catenin transcriptional activity, or whether the pathways bifurcate at this point, resulting in ILK activating the β-catenin pathway, whereas PKB may target other pathways such as P70S6Kinase and control of protein translation or the inactivation of BAD, a pro-apoptotic BcL-2 family member.

EXAMPLE 14

ILK Antisense Oligonucleotides

Antisense oligonucleotides are capable of attenuating the expression of specific genes in vivo by anealing to their RNA transcript and preventing transcription. As such, these oligonucleotides are valuable tools in biological studies of gene function and well as therapeutic agents against human diseases caused by overexpression of specific genes.

The following methods describe an in vitro assay useful in determining the ability of specific antisense oligonucleotides to anneal to an RNA transcript and mediate its cleavage by RNAse H. This "RNAse H" assay consists of three components: 1. an RNA transcript produced in vitro; 2. an antisense oligonucleotide, approximately 19 mer in length, complementary to a region of the RNA transcript; 3. the enzyme RNAse H, which cleaves RNA only at RNA-DNA duplexes. Cleavage is determined by agarose gel electrophoresis of the assay products. This assay will identify antisense oligonucleotides that have the ability to anneal to regions of the RNA transcript thus identifying these regions as having an accessible secondary structure. A series of oligonucleotides scanning the entire ILK cDNA were designed and tested using the RNAse H assay. This identified a limited number of oligonucleotides that were effective in mediating cleavage of the RNA transcript. These selected oligonucleotides were then tested for their efficacy in attenuating ILK expression in a cell culture based assay.

Materials and Methods

Solutions and Buffers

Standard procedures for controlling RNAse contamination were adopted such as the use of rubber gloves, segregated ACS or molecular biology grade reagents, RNAse free pre-packed pipette tips, and baked glassware (Sambrook et al 1989).

Solutions and buffers were prepared using Millipore Milli-Q PF grade water. Diethyl pyrocarbonate (DEPC) treated water and buffers were prepared by adding diethyl pyrocarbonate (Sigma D5758) to a final concentration of 0.1%, mixing, and then incubating at 37° C. for 12 hours. The solutions were then autoclaved at 1.20° C. and 20 psi for 20 min. Solutions of 1 M dithiothreitol (DTT, BDH 3860), 0.5 M ethylenediaminetetraacetate disodium salt (EDTA; Sigma E5134) DEPC treated, 1 M magnesium chloride hexahydrate (Sigma M2670) DEPC treated, 3 M sodium acetate trihydrate (BDH 7610) pH 5.7 DEPC treated, 5 M sodium chloride (BDH 7710) DEPC treated, 10 M sodium hydroxide (Sigma S0899), and 1 M Tris pH 8.0 or 7.4 (BDH 9210) were prepared following Sambrook et al 1989.

One liter of 5×MOPS buffer (0.2 M MOPS pH 7.0, 50 mM sodium acetate, 5 mM EDTA) was prepared by adding 16.6 ml of 3 M sodium acetate pH 5.7 (described above) to 800 ml of Mill-Q PF water, and then adding 41.2 g of 3-(N-morpholino) propanesulfonic acid (MOPS, BDH 6310). The pH was adjusted to 7.0 using 10 M NaOH (described above). Then, 10 ml of 0.5 M EDTA pH 8.0 (described above) was added and volume was adjust to 1000 ml. This was then vacuum filter sterilized through a 0.2 micron plastic disposable filter. MOPS solutions should not be autoclaved but can be stored at room temperature wrapped in foil.

One liter of 5×TBE buffer (0.45 M Tris-borate, 0.01 M EDTA) was prepared by dissolving 54 g of Tris base (BDH 9210) and 27.5 g of boric acid (Sigma B6768) in 800 ml of Mill-Q PF water. Then 20 ml of 0.5 M EDTA DEPC treated (described above) was added and the volume adjusted to 1000 ml. Autoclaving was not required.

RNA sample buffer (66% formamide, 20% formaldehyde, and 0.65×MOPS buffer) was made by mixing 10 ml of deionized formamide (BDH 4610), 3.5 ml of 37% formaldehyde (Aldrich 25, 254-9), and 2.0 ml of 5×MOPS buffer (described above). This can be stored at −20° C. for up to 6 months. The 10× RNA loading buffer (50% gylcerol, 1 mM EDTA, 0.4% xylene cyanol and 2 mg/ml of ethidium bromide was prepared my mixing 5 ml of glycerol (BDH 4750), 20 ul of 0.5 M EDTA DEPC treated (described above), 40 mg of xylene cyanol FF (BDH 9710), 2 ml of 10 mg/ml ethidium bromide solution (BDH 4410), and 3.0 ml of Milli-Q PF water.

Preparation of DNA Oligonucleotides and RNA Transcripts

Phosphodiester oligodeoxynucleotides were produced on an Applied Biosystems 394 synthesizer using standard phosphoramidite chemistry. Antisense oligonucleotides were designed as an almost contiguous head-to-tail series, scanning the entire ILK cDNA, including its 3' and 5' untranslated regions.

In vitro RNA transcripts of ILK cDNA were produced with the Promega RiboMax Large Scale RNA Production System T7 and cDNA template derived from the plasmid ILK13/pRC/CMV (Hannigan et al 1996) linerized at Xba I. The crude RNA transcript was purified using a Qiagen RNeasy mini spin kit.

RNAse H Assay

Phosphodiester antisense oligonucleotides were diluted to 100 nM in hybridization buffer (10 mM Tris pH 7.3, 50 mM NaCl, 5 mM $MgCl_2$), denatured by heating to 90° C. for 2 min, and quick chilled on ice. Then, 5 ul of denatured oligonucleotide was added to wells of a GeNunc 120 ul well module (Nunc 2-32549). The purified ILK RNA transcript was diluted in hybridization buffer to a concentration of 2 uM, heated to 90° C. in a water filled aluminum heat block for 1 min, and then slowly cooled to 37° C. over a period of 30 min. Then, 5 ul of the reannealed RNA transcript was aliquoted to wells of the GeNunc module containing the antisense oligonucleotides. These were hybridized at 37° C. for 4 hr. After this, 1 ul of 10 mM DTT (described above) and 0.5 U of RNAse H (Gibco BRL 18021-014) were added to each well and further incubated at 37° C. for 20 min. The RNAse H cleavage was stopped by adding 30 ul of RNA sample buffer (described above) and 5 ul of 10× RNA loading buffer (described above). The assay products could be stored at −20° C. at this point. Prior to electrophoresis the samples were denatured by heating to 70° C. for 10 min and then cooled to room temperature. Electrophoresis was carried out on Gibco BRL Horizon 1.1×14 apparatus using 20 well combs, 1% agarose (BDH 2120) with 0.5 ug/ml ethidium bromide in the agarose and 0.5×TBE running buffer. The ethidium bromide stained RNA bands were visualized on a UV transilluminator using a BioRad Gel Doc apparatus and MultiAnalyst 1.1 software.

Cell Based Oligonucleotide Transfection

Phosphorothioate antisense oligonucleotides were diluted to 100 uM in Milli-Q PF water. Transfections of oligonucleotides were carried out in a 96 well microtire plate format (Corning Cell Wells 25860) using the following parameters: 1.25 uM oligonucleotide final concentration in the media, 50% confluent IEC18-13 cells (rat intestinal cells stably overexpression ILK; Hannigan et al. 1996), (-MEM media (Gibco BRL 12000-014), and the transfection reagent Fugene 6 (Boehringer/Roche 1 814 443) used according to the directions of the manufacturer. The cells were then incubated at 37° C. and 5% $CO_2$ for 20 to 24 hrs before, a 3H-thymidine incorporation assay was performed on the transfected cells by adding 1 uCi of thymidine-methyl-3H (Sigma 32,222-9) to each well and incubating a further at 37° C. and 5% $CO_2$ for 4 hrs. The 3H-thymidine media was then removed and the cells were washed once with 100 ul per well of phosphate buffered saline pH 7.4 (PBS) and allowed to dry. Then, 100 ul of scintillation fluid was added to each well and the beta emissions were recorded using a Wallac Micro-beta counter.

| | | |
|---|---|---|
| SEQ ID NO 3 | CGTCCATAGCAGCGTCCCG | ILK16345 |
| SEQ ID NO 4 | CCCGTGGTAGCAGTCGAC | ILK2811 |
| SEQ ID NO 5 | CCTTCTCCGGGGAACTCCC | ILK4426 |
| SEQ ID NO 6 | CGGGACTCGGGCTGCAGGA | ILK6446 |
| SEQ ID NO 7 | GCTTTATCCTCGGGACTCG | ILK7456 |
| SEQ ID NO 8 | GGGAAGGAGGATGAACCCC | ILK9577 |
| SEQ ID NO 9 | GCCTGAGGACTGTGGAGTG | ILK11901 |
| SEQ ID NO 10 | GGGGAAGCCTGAGGACTG | ILK12508 |

-continued

| | | |
|---|---|---|
| SEQ ID NO 11 | GAGTGAAAATGTCGTCCAT | ILK17557 |
| SEQ ID NO 12 | AACGGCGACTGCGTTGCCC | ILK20486 |
| SEQ ID NO 13 | TGTTGTCCAGCCACAGGCG | ILK22305 |
| SEQ ID NO 14 | TGGTTGAGGTCGTTCTCCG | ILK24224 |
| SEQ ID NO 15 | GAAGCCATGATCGTCCCCC | ILK26143 |
| SEQ ID NO 16 | CAGGCCCAGTGCAAGGGGG | ILK28163 |
| SEQ ID NO 17 | CGGCCCTCTCGGCAGGCCC | ILK29375 |
| SEQ ID NO 18 | CCACAGCAGAGCGGCCCTC | ILK30486 |
| SEQ ID NO 19 | CCGCATGATCAACATCTC | ILK32407 |
| SEQ ID NO 20 | TTGATCCGTGCCCCCCGC | ILK33821 |
| SEQ ID NO 21 | CATCCCCACGGTTCATTAC | ILK35840 |
| SEQ ID NO 22 | GGGGGTGTCATCCCCACGG | ILK36648 |
| SEQ ID NO 23 | GGCTGCCAGATGCAGGGGG | ILK38163 |
| SEQ ID NO 24 | ATATCACGGTGTCCATGAC | ILK40183 |
| SEQ ID NO 25 | ACTGCAATAGCTTCTGTAC | ILK42103 |
| SEQ ID NO 26 | CACTGCATTGATGTCTGCC | ILK44426 |
| SEQ ID NO 27 | GGGGCACATTCCCGTGTTC | ILK46648 |
| SEQ ID NO 28 | CCAAAAACAGGCATAGTGC | ILK48668 |
| SEQ ID NO 29 | GCCACTTGATCTTGGCCCC | ILK50385 |
| SEQ ID NO 30 | CATTTGCCACCAGGTCCTC | ILK52305 |
| SEQ ID NO 31 | AGATGCTGACAAGGGCCCC | ILK54123 |
| SEQ ID NO 32 | ATCTCTCCATACTTGTTAC | ILK56042 |
| SEQ ID NO 33 | CTTGGCTTTGTCCACAGGC | ILK57961 |
| SEQ ID NO 34 | AAGCTCTCTCAGGGGTGCC | ILK59779 |
| SEQ ID NO 35 | TCTCTGCCCGCTCTCGGAG | ILK61698 |
| SEQ ID NO 36 | CGGTTGAGATTCTGGCCCA | ILK63820 |
| SEQ ID NO 37 | AGAATGTGTCCTTGTATGG | ILK66143 |
| SEQ ID NO 38 | GTGCGGGTGGTCCCCTTCC | ILK68062 |
| SEQ ID NO 39 | CGGGGCCGAGTGCGGGTGG | ILK68971 |
| SEQ ID NO 40 | GGGTTCCATTTCGGGGCCG | ILK70082 |
| SEQ ID NO 41 | CCAGAGTGTTTGTTCAGGG | ILK71698 |
| SEQ ID NO 42 | AGTTAAGCTGTTTGAAGTC | ILK73921 |
| SEQ ID NO 43 | CTCGTTGAGCTTCGTCAGG | ILK75941 |
| SEQ ID NO 44 | TCCATAGCTCTCCAGAGTG | ILK78163 |
| SEQ ID NO 45 | GCCCTGCCAGCGGCCCTTC | ILK79880 |
| SEQ ID NO 46 | GCACCTTCACGACAATGTC | ILK80220 |
| SEQ ID NO 47 | ACTCCAGTCTCGAACCTTC | ILK84022 |
| SEQ ID NO 48 | AAGTCCCTGCTCTTCCTTG | ILK86042 |
| SEQ ID NO 49 | GCCGGGGACACTCTTCATTG | ILK88061 |
| SEQ ID NO 50 | TCCTGAGCCGGGGACACTC | ILK88668 |

-continued

| | | |
|---|---|---|
| SEQ ID NO 51 | GAGCACATTTGGATGCGAG | ILK90991 |
| SEQ ID NO 52 | GGCAGGCACCTAGCACTGG | ILK92810 |
| SEQ ID NO 53 | ATGAGGAGCAGGTGGAGAC | ILK94830 |
| SEQ ID NO 54 | AGTGTGTGATGAGAGTAGG | ILK96749 |
| SEQ ID NO 55 | AGGGATCCATACGGCATCC | ILK98668 |
| SEQ ID NO 56 | TTCATGTAGTACATTGTAG | ILK100587 |
| SEQ ID NO 57 | CCACGACGAAATTGGTGCC | ILK102406 |
| SEQ ID NO 58 | TTCACAGCCTGGCTCTGGT | ILK104325 |
| SEQ ID NO 59 | TGCCATGTCCAAAGCAAAC | ILK106244 |
| SEQ ID NO 60 | GTAGGAAGGCCATGCCCCT | ILK108163 |
| SEQ ID NO 61 | ATGAGGGGCTCTAGTGTGT | ILK110082 |
| SEQ ID NO 62 | ATTGAGTGCATGTCGTGGG | ILK111901 |
| SEQ ID NO 63 | CAATCATTACACTACGGCT | ILK113820 |
| SEQ ID NO 64 | TTCGGGCAGTCATGTCCTC | ILK115941 |
| SEQ ID NO 65 | AACTTGACATCAGCCATGC | ILK118163 |
| SEQ ID NO 66 | ACCAGGACATTGGAAAGAG | ILK120082 |
| SEQ ID NO 67 | AGGCAGGTGCATACATGCG | ILK121901 |
| SEQ ID NO 68 | CGGGGGCTACCCAGGCAGG | ILK123113 |
| SEQ ID NO 69 | AGAGCTTCGGGGGCTACCC | ILK123820 |
| SEQ ID NO 70 | GTCTTCAGGCTTCTTCTGC | ILK125739 |
| SEQ ID NO 71 | TCTGCTGAGCGTCTGTTTG | ILK127759 |
| SEQ ID NO 72 | GCACTGCAAAACTCCACATG | ILK129778 |
| SEQ ID NO 73 | GTGTCACCAGTTCCCACAG | ILK131800 |
| SEQ ID NO 74 | GGGTACCTCCCGTGTCACC | ILK132911 |
| SEQ ID NO 75 | CCATATTGGAGAGGTCAGC | ILK135133 |
| SEQ ID NO 76 | GGCCTTCCAATGCCACCTT | ILK138163 |
| SEQ ID NO 77 | GGTGGGATGGTAGGCCGAA | ILK140082 |
| SEQ ID NO 78 | CACATGAGGGGAAATACCT | ILK141901 |
| SEQ ID NO 79 | CATGCAGATCTTCATGAGC | ILK144325 |
| SEQ ID NO 80 | GGGTCGCTTTGCAGGGTCT | ILK146749 |
| SEQ ID NO 81 | GGATAGGCACAATCATGTC | ILK149274 |
| SEQ ID NO 82 | ACTTGTCCTGCATCTTCTC | ILK151395 |
| SEQ ID NO 83 | GGCAAGGACCTTCCAGTCC | ILK153315 |
| SEQ ID NO 84 | CCCGACACCTCTGGAGTTC | ILK155335 |
| SEQ ID NO 85 | GTGCATTCCCCCAACCATG | ILK157355 |
| SEQ ID NO 86 | GGGGAGGTGCATTCCCCC | ILK157962 |
| SEQ ID NO 87 | GGCCTGCTGCTTTGGGGAGG | ILK159273 |
| SEQ ID NO 88 | GCAACCAGAGGCCTGCTGC | ILK160183 |
| SEQ ID NO 89 | GGAGGCGGGGAGGCAACC | ILK161496 |
| SEQ ID NO 90 | CCATGACTGGAGGCGGGGG | ILK162204 |

-continued

| SEQ ID NO 91 | ATGGACCCCAGGCTGGGGT | ILK164527 |
| SEQ ID NO 92 | GGGGGAAGGGGATGGACCCC | ILK165637 |
| SEQ ID NO 93 | GGTAGGGATGGGGAAGGGG | ILK166546 |
| SEQ ID NO 94 | CCCGCCCCTCTTGCGCACAG | ILK168667 |
| SEQ ID NO 95 | GCTCTGAGCCCGCCCCTC | ILK169477 |
| SEQ ID NO 96 | GACACCATGTGGCAAGTGAC | ILK171798 |
| SEQ ID NO 97 | GCTGATCCCTCCCATGTTGG | ILK173920 |
| SEQ ID NO 98 | GGCGGGGCTGATCCCTCCC | ILK174527 |
| SEQ ID NO 99 | TAATAAACTTTATTGTGAC | ILK176547 |

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

What is claimed is:

1. An isolated polynucleotide consisting of at least 12 contiguous nucleotides of the sequence set forth in SEQ ID NO:100.

2. The isolated polynucleotide of claim 1, and a pharmaceutically acceptable carrier.

3. An isolated polynucleotide consisting of at least 18 contiguous nucleotides of the sequence set forth in SEQ ID NO:100.

4. The isolated polynucleotide of claim 3, wherein the polynucleotide is DNA.

5. The isolated polynucleotide of claim 3, wherein the polynucleotide is RNA.

6. The isolated polynucleotide of claim 3, wherein the polynucleotide is double-stranded.

7. The isolated polynucleotide of claim 3, wherein the polynucleotide is single-stranded.

8. The isolated polynucleotide of claim 7, wherein said polynucleotide is complementary to the sequence set forth in SEQ ID NO:100.

9. The isolated polynucleotide of claim 8, wherein the polynucleotide comprises at least 20 contiguous nucleotides.

10. The isolated polynucleotide claim 8, wherein the at least 18 contiguous nucleotides is complementary to the 5' untranslated region of SEQ ID NO:100, residues 1-156.

11. The isolated polynucleotide of claim 8, wherein the at least 18 contiguous nucleotides is complementary to the coding sequence of SEQ ID NO:100, residues 157-1509.

12. A composition containing the isolated polynucleotide of claim 8 and a pharmaceutically acceptable carrier.

13. The isolated polynucleotide of claim 3, wherein the at least 18 contiguous nucleotides is within the coding sequence of SEQ ID NO:100.

14. The isolated polynucleotide of claim 3, wherein the at least 18 contiguous nucleotides is within the 5' untranslated region of SEQ ID NO:100.

15. The isolated polynucleotide of claim 3, wherein the at least 18 contiguous nucleotides is within the 5' untranslated region of SEQ ID NO:100 or the coding sequence of SEQ ID NO:100.

16. The isolated polynucleotide of claim 3, and a pharmaceutically acceptable carrier.

17. An isolated polynucleotide consisting of at least 18 contiguous nucleotides complementary to the sequence set forth in SEQ ID NO:100 wherein the polynucleotide contains at least one phosphorothioate linkage in the backbone of the polynucleotide.

18. A composition containing the isolated polynucleotide of claim 17, and a pharmaceutically acceptable carrier.

19. An isolated polynucleotide consisting of at least 18 contiguous nucleotides complementary to the sequence set forth in SEQ ID NO:100 wherein the polynucleotide contains at least one 2'-O-methyl ribose sugar in the backbone of the polynucleotide.

20. A composition containing the isolated polynucleotide of claim 19, and a pharmaceutically acceptable carrier.

21. An isolated polynucleotide consisting of at least 18 contiguous nucleotides complementary to the sequence set forth in SEQ ID NO:100 wherein the polynucleotide contains at least one modified heterocyclic nucleobase, which modified heterocyclic nucleobase maintains proper base pairing.

22. A composition containing the isolated polynucleotide of claim 21, and a pharmaceutically acceptable carrier.

23. An isolated polynucleotide consisting of at least 18 contiguous nucleotides complementary to the sequence set forth in SEQ ID NO:100 wherein the polynucleotide phosphodiester backbone is chemically modified from the native phosphodiester structure to increase stability, but maintains proper base pairing.

24. A composition containing the isolated polynucleotide of claim 23, and a pharmaceutically acceptable carrier.

* * * * *

SEQUENCE LISTING

<160> NUMBER OF SEQ ID NOS: 101

<210> SEQ ID NO 1
<211> LENGTH: 1789
<212> TYPE: DNA
<213> ORGANISM: Homo sapiens

<400> SEQUENCE: 1

```
gaattcatct gtcgactgct accacgggag ttccccggag aaggatcctg cagcccgagt      60
cccgaggata aagcttgggg ttcatcctcc ttccctggat cactccacag tcctcaggct     120
tccccaatcc aggggactcg gcgccgggac gctgct atg gac gac att ttc act        174 cag tgc cgg gag ggc aac gca gtc gcc gtt cgc ctg tgg ctg gac aac        222 acg gag aac gac ctc aac cag ggg gac gat cat ggc ttc tcc ccc ttg        270 cac tgg gcc tgc cga gag ggc cgc tct gct gtg gtt gag atg ttg atc        318 atg cgg ggg gca cgg atc aat gta atg aac cgt ggg gat gac acc ccc        366 ctg cat ctg gca gcc agt cat gga cac cgt gat att gta cag aag cta        414 ttg cag tac aag gca gac atc aat gca gtg aat gaa cac ggg aat gtg        462 ccc ctg cac tat gcc tgt ttt tgg ggc caa gat caa gtg gca gag gac        510 ctg gtg gca aat ggg gcc ctt gtc agc atc tgt aac aag tat gga gag        558 atg cct gtg gac aaa gcc aag gca ccc ctg aga gag ctt ctc cga gag        606 cgg gca gag aag atg ggc cag aat ctc aac cgt att cca tac aag gac        654 aca ttc tgg aag ggg acc acc cgc act cgg ccc cga aat gga acc ctg        702 aac aaa cac tct ggc att gac ttc aaa cag ctt aac ttc ctg acg aag        750 ctc aac gag aat cac tct gga gag cta tgg aag ggc cgc tgg cag ggc        798 aat gac att gtc gtg aag gtg ctg aag gtt cga gac tgg agt aca agg        846 aag agc agg gac ttc aat gaa gag tgt ccc cgg ctc agg att ttc tcg        894 cat cca aat gtg ctc cca gtg cta ggt gcc tgc cag tct cca cct gct        942 cct cat cct act ctc atc aca cac tgg atg ccg tat gga tcc ctc tac        990 aat gta cta cat gaa ggc acc aat ttc gtc gtg gac cag agc cag gct       1038 gtg aag ttt gct ttg gac atg gca agg ggc atg gcc ttc cta cac aca       1086
```

```
cta gag ccc ctc atc cca cga cat gca ctc aat agc cgt agt gta atg    1134
att gat gag gac atg act gcc cga att agc atg gct gat gtc aag ttc    1182
tct ttc caa tgt cct ggt cgc atg tat gca cct gcc tgg gta gcc ccc    1230
gaa gct ctg cag aag aag cct gaa gac aca aac aga cgc tca gca gac    1278
atg tgg agt ttt gca gtg ctt ctg tgg gaa ctg gtg aca cgg gag gta    1326
ccc ttt gct gac ctc tcc aat atg gag att gga atg aag gtg gca ttg    1374
gaa ggc ctt cgg cct acc atc cca cca ggt att tcc cct cat gtg tgt    1422
aag ctc atg aag atc tgc atg aat gaa gac cct gca aag cga ccc aaa    1470
ttt gac atg att gtg cct atc ctt gag aag atg cag gac aag            1512
taggactgga aggtccttgc ctgaactcca gaggtgtcgg acatggttg ggggaatgca    1572
cctccccaaa gcagcaggcc tctggttgcc tcccccgcct ccagtcatgg tactacccca   1632
gcctggggtc catccccttc ccccatccct accactgtgc gcaagagggg cgggctcaga   1692
gctttgtcac ttgccacatg gtgtctccca acatgggagg gatcagcccc gcctgtcaca   1752
ataaagttta ttatgaaaaa aaaaaaaaaa aaaaaaa                            1789
```

<210> SEQ ID NO 2
<211> LENGTH: 452
<212> TYPE: PRT
<213> ORGANISM: Homo sapiens

<400> SEQUENCE: 2

```
Met Asp Asp Ile Phe Thr Gln Cys Arg Glu Gly Asn Ala Val Ala Val
  1               5                  10                  15

Arg Leu Trp Leu Asp Asn Thr Glu Asn Asp Leu Asn Gln Gly Asp Asp
             20                  25                  30

His Gly Phe Ser Pro Leu His Trp Ala Cys Arg Glu Gly Arg Ser Ala
         35                  40                  45

Val Val Glu Met Leu Ile Met Arg Gly Ala Arg Ile Asn Val Met Asn
     50                  55                  60

Arg Gly Asp Asp Thr Pro Leu His Leu Ala Ala Ser His Gly His Arg
 65                  70                  75                  80

Asp Ile Val Gln Lys Leu Leu Gln Tyr Lys Ala Asp Ile Asn Ala Val
                 85                  90                  95

Asn Glu His Gly Asn Val Pro Leu His Tyr Ala Cys Phe Trp Gly Gln
            100                 105                 110

Asp Gln Val Ala Glu Asp Leu Val Ala Asn Gly Ala Leu Val Ser Ile
        115                 120                 125

Cys Asn Lys Tyr Gly Glu Met Pro Val Asp Lys Ala Lys Ala Pro Leu
    130                 135                 140

Arg Glu Leu Leu Arg Glu Arg Ala Glu Lys Met Gly Gln Asn Leu Asn
145                 150                 155                 160

Arg Ile Pro Tyr Lys Asp Thr Phe Trp Lys Gly Thr Thr Arg Thr Arg
                165                 170                 175

Pro Arg Asn Gly Thr Leu Asn Lys His Ser Gly Ile Asp Phe Lys Gln
            180                 185                 190

Leu Asn Phe Leu Thr Lys Leu Asn Glu Asn His Ser Gly Glu Leu Trp
        195                 200                 205

Lys Gly Arg Trp Gln Gly Asn Asp Ile Val Val Lys Val Leu Lys Val
    210                 215                 220
```

```
Arg Asp Trp Ser Thr Arg Lys Ser Arg Asp Phe Asn Glu Glu Cys Pro
225                 230                 235                 240

Arg Leu Arg Ile Phe Ser His Pro Asn Val Leu Pro Val Leu Gly Ala
            245                 250                 255

Cys Gln Ser Pro Pro Ala Pro His Pro Thr Leu Ile Thr His Trp Met
        260                 265                 270

Pro Tyr Gly Ser Leu Tyr Asn Val Leu His Glu Gly Thr Asn Phe Val
    275                 280                 285

Val Asp Gln Ser Gln Ala Val Lys Phe Ala Leu Asp Met Ala Arg Gly
290                 295                 300

Met Ala Phe Leu His Thr Leu Glu Pro Leu Ile Pro Arg His Ala Leu
305                 310                 315                 320

Asn Ser Arg Ser Val Met Ile Asp Glu Asp Met Thr Ala Arg Ile Ser
                325                 330                 335

Met Ala Asp Val Lys Phe Ser Phe Gln Cys Pro Gly Arg Met Tyr Ala
                340                 345                 350

Pro Ala Trp Val Ala Pro Glu Ala Leu Gln Lys Lys Pro Glu Asp Thr
            355                 360                 365

Asn Arg Arg Ser Ala Asp Met Trp Ser Phe Ala Val Leu Leu Trp Glu
370                 375                 380

Leu Val Thr Arg Glu Val Pro Phe Ala Asp Leu Ser Asn Met Glu Ile
385                 390                 395                 400

Gly Met Lys Val Ala Leu Glu Gly Leu Arg Pro Thr Ile Pro Pro Gly
                405                 410                 415

Ile Ser Pro His Val Cys Lys Leu Met Lys Ile Cys Met Asn Glu Asp
                420                 425                 430

Pro Ala Lys Arg Pro Lys Phe Asp Met Ile Val Pro Ile Leu Glu Lys
            435                 440                 445

Met Gln Asp Lys
    450

<210> SEQ ID NO 3
<211> LENGTH: 19
<212> TYPE: DNA
<213> ORGANISM: Homo sapiens

<400> SEQUENCE: 3
cgtccatagc agcgtcccg                                             19

<210> SEQ ID NO 4
<211> LENGTH: 18
<212> TYPE: DNA
<213> ORGANISM: Homo sapiens

<400> SEQUENCE: 4
cccgtggtag cagtcgac                                              18

<210> SEQ ID NO 5
<211> LENGTH: 19
<212> TYPE: DNA
<213> ORGANISM: Homo sapiens

<400> SEQUENCE: 5
ccttctccgg ggaactccc                                             19

<210> SEQ ID NO 6
<211> LENGTH: 19
<212> TYPE: DNA
```

```
<213> ORGANISM: Homo sapiens

<400> SEQUENCE: 6
cgggactcgg gctgcagga                                              19

<210> SEQ ID NO 7
<211> LENGTH: 19
<212> TYPE: DNA
<213> ORGANISM: Homo sapiens

<400> SEQUENCE: 7
gctttatcct cgggactcg                                              19

<210> SEQ ID NO 8
<211> LENGTH: 19
<212> TYPE: DNA
<213> ORGANISM: Homo sapiens

<400> SEQUENCE: 8
gggaaggagg atgaacccc                                              19

<210> SEQ ID NO 9
<211> LENGTH: 19
<212> TYPE: DNA
<213> ORGANISM: Homo sapiens

<400> SEQUENCE: 9
gcctgaggac tgtggagtg                                              19

<210> SEQ ID NO 10
<211> LENGTH: 18
<212> TYPE: DNA
<213> ORGANISM: Homo sapiens

<400> SEQUENCE: 10
ggggaagcct gaggactg                                               18

<210> SEQ ID NO 11
<211> LENGTH: 19
<212> TYPE: DNA
<213> ORGANISM: Homo sapiens

<400> SEQUENCE: 11
gagtgaaaat gtcgtccat                                              19

<210> SEQ ID NO 12
<211> LENGTH: 19
<212> TYPE: DNA
<213> ORGANISM: Homo sapiens

<400> SEQUENCE: 12
aacggcgact gcgttgccc                                              19

<210> SEQ ID NO 13
<211> LENGTH: 19
<212> TYPE: DNA
<213> ORGANISM: Homo sapiens

<400> SEQUENCE: 13
tgttgtccag ccacaggcg                                              19

<210> SEQ ID NO 14
<211> LENGTH: 19
```

```
<212> TYPE: DNA
<213> ORGANISM: Homo sapiens

<400> SEQUENCE: 14
tggttgaggt cgttctccg                                                19

<210> SEQ ID NO 15
<211> LENGTH: 19
<212> TYPE: DNA
<213> ORGANISM: Homo sapiens

<400> SEQUENCE: 15
gaagccatga tcgtccccc                                                19

<210> SEQ ID NO 16
<211> LENGTH: 19
<212> TYPE: DNA
<213> ORGANISM: Homo sapiens

<400> SEQUENCE: 16
caggcccagt gcaaggggg                                                19

<210> SEQ ID NO 17
<211> LENGTH: 19
<212> TYPE: DNA
<213> ORGANISM: Homo sapiens

<400> SEQUENCE: 17
cggccctctc ggcaggccc                                                19

<210> SEQ ID NO 18
<211> LENGTH: 19
<212> TYPE: DNA
<213> ORGANISM: Homo sapiens

<400> SEQUENCE: 18
ccacagcaga gcggccctc                                                19

<210> SEQ ID NO 19
<211> LENGTH: 18
<212> TYPE: DNA
<213> ORGANISM: Homo sapiens

<400> SEQUENCE: 19
ccgcatgatc aacatctc                                                 18

<210> SEQ ID NO 20
<211> LENGTH: 18
<212> TYPE: DNA
<213> ORGANISM: Homo sapiens

<400> SEQUENCE: 20
ttgatccgtg cccccccgc                                                18

<210> SEQ ID NO 21
<211> LENGTH: 19
<212> TYPE: DNA
<213> ORGANISM: Homo sapiens

<400> SEQUENCE: 21
catccccacg gttcattac                                                19

<210> SEQ ID NO 22
```

-continued

```
<211> LENGTH: 19
<212> TYPE: DNA
<213> ORGANISM: Homo sapiens

<400> SEQUENCE: 22
gggggtgtca tccccacgg                                              19

<210> SEQ ID NO 23
<211> LENGTH: 19
<212> TYPE: DNA
<213> ORGANISM: Homo sapiens

<400> SEQUENCE: 23
ggctgccaga tgcaggggg                                              19

<210> SEQ ID NO 24
<211> LENGTH: 19
<212> TYPE: DNA
<213> ORGANISM: Homo sapiens

<400> SEQUENCE: 24
atatcacggt gtccatgac                                              19

<210> SEQ ID NO 25
<211> LENGTH: 19
<212> TYPE: DNA
<213> ORGANISM: Homo sapiens

<400> SEQUENCE: 25
actgcaatag cttctgtac                                              19

<210> SEQ ID NO 26
<211> LENGTH: 19
<212> TYPE: DNA
<213> ORGANISM: Homo sapiens

<400> SEQUENCE: 26
cactgcattg atgtctgcc                                              19

<210> SEQ ID NO 27
<211> LENGTH: 19
<212> TYPE: DNA
<213> ORGANISM: Homo sapiens

<400> SEQUENCE: 27
ggggcacatt cccgtgttc                                              19

<210> SEQ ID NO 28
<211> LENGTH: 19
<212> TYPE: DNA
<213> ORGANISM: Homo sapiens

<400> SEQUENCE: 28
ccaaaaacag gcatagtgc                                              19

<210> SEQ ID NO 29
<211> LENGTH: 19
<212> TYPE: DNA
<213> ORGANISM: Homo sapiens

<400> SEQUENCE: 29
gccacttgat cttggcccc                                              19
```

```
<210> SEQ ID NO 30
<211> LENGTH: 19
<212> TYPE: DNA
<213> ORGANISM: Homo sapiens

<400> SEQUENCE: 30
catttgccac caggtcctc                                                   19

<210> SEQ ID NO 31
<211> LENGTH: 19
<212> TYPE: DNA
<213> ORGANISM: Homo sapiens

<400> SEQUENCE: 31
agatgctgac aagggcccc                                                   19

<210> SEQ ID NO 32
<211> LENGTH: 19
<212> TYPE: DNA
<213> ORGANISM: Homo sapiens

<400> SEQUENCE: 32
atctctccat acttgttac                                                   19

<210> SEQ ID NO 33
<211> LENGTH: 19
<212> TYPE: DNA
<213> ORGANISM: Homo sapiens

<400> SEQUENCE: 33
cttggctttg tccacaggc                                                   19

<210> SEQ ID NO 34
<211> LENGTH: 19
<212> TYPE: DNA
<213> ORGANISM: Homo sapiens

<400> SEQUENCE: 34
aagctctctc aggggtgcc                                                   19

<210> SEQ ID NO 35
<211> LENGTH: 19
<212> TYPE: DNA
<213> ORGANISM: Homo sapiens

<400> SEQUENCE: 35
tctctgcccg ctctcggag                                                   19

<210> SEQ ID NO 36
<211> LENGTH: 19
<212> TYPE: DNA
<213> ORGANISM: Homo sapiens

<400> SEQUENCE: 36
cggttgagat tctggccca                                                   19

<210> SEQ ID NO 37
<211> LENGTH: 19
<212> TYPE: DNA
<213> ORGANISM: Homo sapiens

<400> SEQUENCE: 37
agaatgtgtc cttgtatgg                                                   19
```

```
<210> SEQ ID NO 38
<211> LENGTH: 19
<212> TYPE: DNA
<213> ORGANISM: Homo sapiens

<400> SEQUENCE: 38
gtgcgggtgg tccccttcc                                                  19

<210> SEQ ID NO 39
<211> LENGTH: 19
<212> TYPE: DNA
<213> ORGANISM: Homo sapiens

<400> SEQUENCE: 39
cggggccgag tgcgggtgg                                                  19

<210> SEQ ID NO 40
<211> LENGTH: 19
<212> TYPE: DNA
<213> ORGANISM: Homo sapiens

<400> SEQUENCE: 40
gggttccatt tcggggccg                                                  19

<210> SEQ ID NO 41
<211> LENGTH: 19
<212> TYPE: DNA
<213> ORGANISM: Homo sapiens

<400> SEQUENCE: 41
ccagagtgtt tgttcaggg                                                  19

<210> SEQ ID NO 42
<211> LENGTH: 19
<212> TYPE: DNA
<213> ORGANISM: Homo sapiens

<400> SEQUENCE: 42
agttaagctg tttgaagtc                                                  19

<210> SEQ ID NO 43
<211> LENGTH: 19
<212> TYPE: DNA
<213> ORGANISM: Homo sapiens

<400> SEQUENCE: 43
ctcgttgagc ttcgtcagg                                                  19

<210> SEQ ID NO 44
<211> LENGTH: 19
<212> TYPE: DNA
<213> ORGANISM: Homo sapiens

<400> SEQUENCE: 44
tccatagctc tccagagtg                                                  19

<210> SEQ ID NO 45
<211> LENGTH: 19
<212> TYPE: DNA
<213> ORGANISM: Homo sapiens

<400> SEQUENCE: 45
gccctgccag cggcccttc                                                  19
```

<210> SEQ ID NO 46
<211> LENGTH: 19
<212> TYPE: DNA
<213> ORGANISM: Homo sapiens

<400> SEQUENCE: 46
gcaccttcac gacaatgtc                                              19

<210> SEQ ID NO 47
<211> LENGTH: 19
<212> TYPE: DNA
<213> ORGANISM: Homo sapiens

<400> SEQUENCE: 47
actccagtct cgaaccttc                                              19

<210> SEQ ID NO 48
<211> LENGTH: 19
<212> TYPE: DNA
<213> ORGANISM: Homo sapiens

<400> SEQUENCE: 48
aagtccctgc tcttccttg                                              19

<210> SEQ ID NO 49
<211> LENGTH: 20
<212> TYPE: DNA
<213> ORGANISM: Homo sapiens

<400> SEQUENCE: 49
gccggggaca ctcttcattg                                             20

<210> SEQ ID NO 50
<211> LENGTH: 19
<212> TYPE: DNA
<213> ORGANISM: Homo sapiens

<400> SEQUENCE: 50
tcctgagccg gggacactc                                              19

<210> SEQ ID NO 51
<211> LENGTH: 19
<212> TYPE: DNA
<213> ORGANISM: Homo sapiens

<400> SEQUENCE: 51
gagcacattt ggatgcgag                                              19

<210> SEQ ID NO 52
<211> LENGTH: 19
<212> TYPE: DNA
<213> ORGANISM: Homo sapiens

<400> SEQUENCE: 52
ggcaggcacc tagcactgg                                              19

<210> SEQ ID NO 53
<211> LENGTH: 19
<212> TYPE: DNA
<213> ORGANISM: Homo sapiens

<400> SEQUENCE: 53

```
atgaggagca ggtggagac                                               19
```

<210> SEQ ID NO 54
<211> LENGTH: 19
<212> TYPE: DNA
<213> ORGANISM: Homo sapiens

<400> SEQUENCE: 54

```
agtgtgtgat gagagtagg                                               19
```

<210> SEQ ID NO 55
<211> LENGTH: 19
<212> TYPE: DNA
<213> ORGANISM: Homo sapiens

<400> SEQUENCE: 55

```
agggatccat acggcatcc                                               19
```

<210> SEQ ID NO 56
<211> LENGTH: 19
<212> TYPE: DNA
<213> ORGANISM: Homo sapiens

<400> SEQUENCE: 56

```
ttcatgtagt acattgtag                                               19
```

<210> SEQ ID NO 57
<211> LENGTH: 19
<212> TYPE: DNA
<213> ORGANISM: Homo sapiens

<400> SEQUENCE: 57

```
ccacgacgaa attggtgcc                                               19
```

<210> SEQ ID NO 58
<211> LENGTH: 19
<212> TYPE: DNA
<213> ORGANISM: Homo sapiens

<400> SEQUENCE: 58

```
ttcacagcct ggctctggt                                               19
```

<210> SEQ ID NO 59
<211> LENGTH: 19
<212> TYPE: DNA
<213> ORGANISM: Homo sapiens

<400> SEQUENCE: 59

```
tgccatgtcc aaagcaaac                                               19
```

<210> SEQ ID NO 60
<211> LENGTH: 19
<212> TYPE: DNA
<213> ORGANISM: Homo sapiens

<400> SEQUENCE: 60

```
gtaggaaggc catgcccct                                               19
```

<210> SEQ ID NO 61
<211> LENGTH: 19
<212> TYPE: DNA
<213> ORGANISM: Homo sapiens

<400> SEQUENCE: 61

```
atgaggggct ctagtgtgt                                                    19

<210> SEQ ID NO 62
<211> LENGTH: 19
<212> TYPE: DNA
<213> ORGANISM: Homo sapiens

<400> SEQUENCE: 62
attgagtgca tgtcgtggg                                                    19

<210> SEQ ID NO 63
<211> LENGTH: 19
<212> TYPE: DNA
<213> ORGANISM: Homo sapiens

<400> SEQUENCE: 63
caatcattac actacggct                                                    19

<210> SEQ ID NO 64
<211> LENGTH: 19
<212> TYPE: DNA
<213> ORGANISM: Homo sapiens

<400> SEQUENCE: 64
ttcgggcagt catgtcctc                                                    19

<210> SEQ ID NO 65
<211> LENGTH: 19
<212> TYPE: DNA
<213> ORGANISM: Homo sapiens

<400> SEQUENCE: 65
aacttgacat cagccatgc                                                    19

<210> SEQ ID NO 66
<211> LENGTH: 19
<212> TYPE: DNA
<213> ORGANISM: Homo sapiens

<400> SEQUENCE: 66
accaggacat tggaaagag                                                    19

<210> SEQ ID NO 67
<211> LENGTH: 19
<212> TYPE: DNA
<213> ORGANISM: Homo sapiens

<400> SEQUENCE: 67
aggcaggtgc atacatgcg                                                    19

<210> SEQ ID NO 68
<211> LENGTH: 19
<212> TYPE: DNA
<213> ORGANISM: Homo sapiens

<400> SEQUENCE: 68
cgggggctac ccaggcagg                                                    19

<210> SEQ ID NO 69
<211> LENGTH: 19
<212> TYPE: DNA
<213> ORGANISM: Homo sapiens
```

<400> SEQUENCE: 69
agagcttcgg gggctaccc                                                19

<210> SEQ ID NO 70
<211> LENGTH: 19
<212> TYPE: DNA
<213> ORGANISM: Homo sapiens

<400> SEQUENCE: 70
gtcttcaggc ttcttctgc                                                19

<210> SEQ ID NO 71
<211> LENGTH: 19
<212> TYPE: DNA
<213> ORGANISM: Homo sapiens

<400> SEQUENCE: 71
tctgctgagc gtctgtttg                                                19

<210> SEQ ID NO 72
<211> LENGTH: 20
<212> TYPE: DNA
<213> ORGANISM: Homo sapiens

<400> SEQUENCE: 72
gcactgcaaa actccacatg                                               20

<210> SEQ ID NO 73
<211> LENGTH: 19
<212> TYPE: DNA
<213> ORGANISM: Homo sapiens

<400> SEQUENCE: 73
gtgtcaccag ttcccacag                                                19

<210> SEQ ID NO 74
<211> LENGTH: 19
<212> TYPE: DNA
<213> ORGANISM: Homo sapiens

<400> SEQUENCE: 74
gggtacctcc cgtgtcacc                                                19

<210> SEQ ID NO 75
<211> LENGTH: 19
<212> TYPE: DNA
<213> ORGANISM: Homo sapiens

<400> SEQUENCE: 75
ccatattgga gaggtcagc                                                19

<210> SEQ ID NO 76
<211> LENGTH: 19
<212> TYPE: DNA
<213> ORGANISM: Homo sapiens

<400> SEQUENCE: 76
ggccttccaa tgccacctt                                                19

<210> SEQ ID NO 77
<211> LENGTH: 19
<212> TYPE: DNA
<213> ORGANISM: Homo sapiens

<400> SEQUENCE: 77
ggtgggatgg taggccgaa                                               19

<210> SEQ ID NO 78
<211> LENGTH: 19
<212> TYPE: DNA
<213> ORGANISM: Homo sapiens

<400> SEQUENCE: 78
cacatgaggg gaaatacct                                               19

<210> SEQ ID NO 79
<211> LENGTH: 19
<212> TYPE: DNA
<213> ORGANISM: Homo sapiens

<400> SEQUENCE: 79
catgcagatc ttcatgagc                                               19

<210> SEQ ID NO 80
<211> LENGTH: 19
<212> TYPE: DNA
<213> ORGANISM: Homo sapiens

<400> SEQUENCE: 80
gggtcgcttt gcagggtct                                               19

<210> SEQ ID NO 81
<211> LENGTH: 19
<212> TYPE: DNA
<213> ORGANISM: Homo sapiens

<400> SEQUENCE: 81
ggataggcac aatcatgtc                                               19

<210> SEQ ID NO 82
<211> LENGTH: 19
<212> TYPE: DNA
<213> ORGANISM: Homo sapiens

<400> SEQUENCE: 82
acttgtcctg catcttctc                                               19

<210> SEQ ID NO 83
<211> LENGTH: 19
<212> TYPE: DNA
<213> ORGANISM: Homo sapiens

<400> SEQUENCE: 83
ggcaaggacc ttccagtcc                                               19

<210> SEQ ID NO 84
<211> LENGTH: 19
<212> TYPE: DNA
<213> ORGANISM: Homo sapiens

<400> SEQUENCE: 84
cccgacacct ctggagttc                                               19

<210> SEQ ID NO 85
<211> LENGTH: 19
<212> TYPE: DNA

```
<213> ORGANISM: Homo sapiens

<400> SEQUENCE: 85
gtgcattccc ccaaccatg                                                  19

<210> SEQ ID NO 86
<211> LENGTH: 18
<212> TYPE: DNA
<213> ORGANISM: Homo sapiens

<400> SEQUENCE: 86
ggggaggtgc attccccc                                                   18

<210> SEQ ID NO 87
<211> LENGTH: 20
<212> TYPE: DNA
<213> ORGANISM: Homo sapiens

<400> SEQUENCE: 87
ggcctgctgc tttggggagg                                                 20

<210> SEQ ID NO 88
<211> LENGTH: 19
<212> TYPE: DNA
<213> ORGANISM: Homo sapiens

<400> SEQUENCE: 88
gcaaccagag gcctgctgc                                                  19

<210> SEQ ID NO 89
<211> LENGTH: 19
<212> TYPE: DNA
<213> ORGANISM: Homo sapiens

<400> SEQUENCE: 89
ggaggcgggg gaggcaacc                                                  19

<210> SEQ ID NO 90
<211> LENGTH: 19
<212> TYPE: DNA
<213> ORGANISM: Homo sapiens

<400> SEQUENCE: 90
ccatgactgg aggcggggg                                                  19

<210> SEQ ID NO 91
<211> LENGTH: 19
<212> TYPE: DNA
<213> ORGANISM: Homo sapiens

<400> SEQUENCE: 91
atggacccca ggctggggt                                                  19

<210> SEQ ID NO 92
<211> LENGTH: 20
<212> TYPE: DNA
<213> ORGANISM: Homo sapiens

<400> SEQUENCE: 92
gggggaaggg gatggacccc                                                 20

<210> SEQ ID NO 93
<211> LENGTH: 20
```

```
<212> TYPE: DNA
<213> ORGANISM: Homo sapiens

<400> SEQUENCE: 93
ggtagggatg ggggaagggg                                               20

<210> SEQ ID NO 94
<211> LENGTH: 20
<212> TYPE: DNA
<213> ORGANISM: Homo sapiens

<400> SEQUENCE: 94
cccgcccctc ttgcgcacag                                               20

<210> SEQ ID NO 95
<211> LENGTH: 18
<212> TYPE: DNA
<213> ORGANISM: Homo sapiens

<400> SEQUENCE: 95
gctctgagcc cgcccctc                                                 18

<210> SEQ ID NO 96
<211> LENGTH: 20
<212> TYPE: DNA
<213> ORGANISM: Homo sapiens

<400> SEQUENCE: 96
gacaccatgt ggcaagtgac                                               20

<210> SEQ ID NO 97
<211> LENGTH: 20
<212> TYPE: DNA
<213> ORGANISM: Homo sapiens

<400> SEQUENCE: 97
gctgatccct cccatgttgg                                               20

<210> SEQ ID NO 98
<211> LENGTH: 19
<212> TYPE: DNA
<213> ORGANISM: Homo sapiens

<400> SEQUENCE: 98
ggcggggctg atccctccc                                                19

<210> SEQ ID NO 99
<211> LENGTH: 19
<212> TYPE: DNA
<213> ORGANISM: Homo sapiens

<400> SEQUENCE: 99
taataaactt tattgtgac                                                19

<210> SEQ ID NO 100
<211> LENGTH: 1786
<212> TYPE: DNA
<213> ORGANISM: H. sapiens
<220> FEATURE:
<221> NAME/KEY: CDS
<222> LOCATION: (157)...(1509)

<400> SEQUENCE: 100
gaattcatct gtcgactgct accacgggag ttccccggag aaggatcctg cagcccgagt   60
```

```
                                        -continued cccgaggata aagcttgggg ttcatcctcc ttccctggat cactccacag tcctcaggct       120
tccccaatcc aggggactcg gcgccgggac gctgct atg gac gac att ttc act        174
                                        Met Asp Asp Ile Phe Thr
                                        1               5 cag tgc cgg gag ggc aac gca gtc gcc gtt cgc ctg tgg ctg gac aac        222
Gln Cys Arg Glu Gly Asn Ala Val Ala Val Arg Leu Trp Leu Asp Asn
            10                  15                  20 acg gag aac gac ctc aac cag ggg gac gat cat ggc ttc tcc ccc ttg        270
Thr Glu Asn Asp Leu Asn Gln Gly Asp Asp His Gly Phe Ser Pro Leu
        25                  30                  35 cac tgg gcc tgc cga gag ggc cgc tct gct gtg gtt gag atg ttg atc        318
His Trp Ala Cys Arg Glu Gly Arg Ser Ala Val Val Glu Met Leu Ile
    40                  45                  50 atg cgg ggg gca cgg atc aat gta atg aac cgt ggg gat gac acc ccc        366
Met Arg Gly Ala Arg Ile Asn Val Met Asn Arg Gly Asp Asp Thr Pro
55                  60                  65                  70 ctg cat ctg gca gcc agt cat gga cac cgt gat att gta cag aag cta        414
Leu His Leu Ala Ala Ser His Gly His Arg Asp Ile Val Gln Lys Leu
                75                  80                  85 ttg cag tac aag gca gac atc aat gca gtg aat gaa cac ggg aat gtg        462
Leu Gln Tyr Lys Ala Asp Ile Asn Ala Val Asn Glu His Gly Asn Val
            90                  95                  100 ccc ctg cac tat gcc tgt ttt tgg ggc caa gat caa gtg gca gag gac        510
Pro Leu His Tyr Ala Cys Phe Trp Gly Gln Asp Gln Val Ala Glu Asp
        105                 110                 115 ctg gtg gca aat ggg gcc ctt gtc agc atc tgt aac aag tat gga gag        558
Leu Val Ala Asn Gly Ala Leu Val Ser Ile Cys Asn Lys Tyr Gly Glu
    120                 125                 130 atg cct gtg gac aaa gcc aag gca ccc ctg aga gag ctt ctc cga gag        606
Met Pro Val Asp Lys Ala Lys Ala Pro Leu Arg Glu Leu Leu Arg Glu
135                 140                 145                 150 cgg gca gag aag atg ggc cag aat ctc aac cgt att cca tac aag gac        654
Arg Ala Glu Lys Met Gly Gln Asn Leu Asn Arg Ile Pro Tyr Lys Asp
                155                 160                 165 aca ttc tgg aag ggg acc acc cgc act cgg ccc cga aat gga acc ctg        702
Thr Phe Trp Lys Gly Thr Thr Arg Thr Arg Pro Arg Asn Gly Thr Leu
            170                 175                 180 aac aaa cac tct ggc att gac ttc aaa cag ctt aac ttc ctg acg aag        750
Asn Lys His Ser Gly Ile Asp Phe Lys Gln Leu Asn Phe Leu Thr Lys
        185                 190                 195 ctc aac gag aat cac tct gga gag cta tgg aag ggc cgc tgg cag ggc        798
Leu Asn Glu Asn His Ser Gly Glu Leu Trp Lys Gly Arg Trp Gln Gly
    200                 205                 210 aat gac att gtc gtg aag gtg ctg aag gtt cga gac tgg agt aca agg        846
Asn Asp Ile Val Val Lys Val Leu Lys Val Arg Asp Trp Ser Thr Arg
215                 220                 225                 230 aag agc agg gac ttc aat gaa gag tgt ccc cgg ctc agg att ttc tcg        894
Lys Ser Arg Asp Phe Asn Glu Glu Cys Pro Arg Leu Arg Ile Phe Ser
                235                 240                 245 cat cca aat gtg ctc cca gtg cta ggt gcc tgc cag tct cca cct gct        942
His Pro Asn Val Leu Pro Val Leu Gly Ala Cys Gln Ser Pro Pro Ala
            250                 255                 260 cct cat cct act ctc atc aca cac tgg atg ccg tat gga tcc ctc tac        990
Pro His Pro Thr Leu Ile Thr His Trp Met Pro Tyr Gly Ser Leu Tyr
        265                 270                 275 aat gta cta cat gaa ggc acc aat ttc gtc gtg gac cag agc cag gct       1038
Asn Val Leu His Glu Gly Thr Asn Phe Val Val Asp Gln Ser Gln Ala
    280                 285                 290
```

```
gtg aag ttt gct ttg gac atg gca agg ggc atg gcc ttc cta cac aca    1086
Val Lys Phe Ala Leu Asp Met Ala Arg Gly Met Ala Phe Leu His Thr
295                 300                 305                 310 cta gag ccc ctc atc cca cga cat gca ctc aat agc cgt agt gta atg    1134
Leu Glu Pro Leu Ile Pro Arg His Ala Leu Asn Ser Arg Ser Val Met
            315                 320                 325 att gat gag gac atg act gcc cga att agc atg gct gat gtc aag ttc    1182
Ile Asp Glu Asp Met Thr Ala Arg Ile Ser Met Ala Asp Val Lys Phe
            330                 335                 340 tct ttc caa tgt cct ggt cgc atg tat gca cct gcc tgg gta gcc ccc    1230
Ser Phe Gln Cys Pro Gly Arg Met Tyr Ala Pro Ala Trp Val Ala Pro
            345                 350                 355 gaa gct ctg cag aag aag cct gaa gac aca aac aga cgc tca gca gac    1278
Glu Ala Leu Gln Lys Lys Pro Glu Asp Thr Asn Arg Arg Ser Ala Asp
360                 365                 370 atg tgg agt ttt gca gtg ctt ctg tgg gaa ctg gtg aca cgg gag gta    1326
Met Trp Ser Phe Ala Val Leu Leu Trp Glu Leu Val Thr Arg Glu Val
375                 380                 385                 390 ccc ttt gct gac ctc tcc aat atg gag att gga atg aag gtg gca ttg    1374
Pro Phe Ala Asp Leu Ser Asn Met Glu Ile Gly Met Lys Val Ala Leu
                395                 400                 405 gaa ggc ctt cgt acc atc cca cca ggt att tcc cct cat gtg tgt aag    1422
Glu Gly Leu Arg Thr Ile Pro Pro Gly Ile Ser Pro His Val Cys Lys
            410                 415                 420 ctc atg aag atc tgc atg aat gaa gac cct gca aag cga ccc aaa ttt    1470
Leu Met Lys Ile Cys Met Asn Glu Asp Pro Ala Lys Arg Pro Lys Phe
            425                 430                 435 gac atg att gtg cct atc ctt gag aag atg cag gac aag taggactgga    1519
Asp Met Ile Val Pro Ile Leu Glu Lys Met Gln Asp Lys
440                 445                 450 aggtccttgc ctgaactcca gaggtgtcgg gacatggttg ggggaatgca cctccccaaa   1579
gcagcaggcc tctggttgcc tcccccgcct ccagtcatgg tactacccca gcctggggtc   1639 catcccttc ccccatccct accactgtgc gcaagagggg cgggctcaga gctttgtcac    1699
ttgccacatg gtgtctccca acatgggagg gatcagcccc gcctgtcaca ataaagttta   1759
ttatgaaaaa aaaaaaaaaa aaaaaaa                                      1786

<210> SEQ ID NO 101
<211> LENGTH: 451
<212> TYPE: PRT
<213> ORGANISM: H. sapiens

<400> SEQUENCE: 101

Met Asp Asp Ile Phe Thr Gln Cys Arg Glu Gly Asn Ala Val Ala Val
1               5                   10                  15

Arg Leu Trp Leu Asp Asn Thr Glu Asn Asp Leu Asn Gln Gly Asp Asp
                20                  25                  30

His Gly Phe Ser Pro Leu His Trp Ala Cys Arg Glu Gly Arg Ser Ala
            35                  40                  45

Val Val Glu Met Leu Ile Met Arg Gly Ala Arg Ile Asn Val Met Asn
        50                  55                  60

Arg Gly Asp Asp Thr Pro Leu His Leu Ala Ala Ser His Gly His Arg
65                  70                  75                  80

Asp Ile Val Gln Lys Leu Leu Gln Tyr Lys Ala Asp Ile Asn Ala Val
                85                  90                  95

Asn Glu His Gly Asn Val Pro Leu His Tyr Ala Cys Phe Trp Gly Gln
            100                 105                 110
```

```
Asp Gln Val Ala Glu Asp Leu Val Ala Asn Gly Ala Leu Val Ser Ile
        115                 120                 125

Cys Asn Lys Tyr Gly Glu Met Pro Val Asp Lys Ala Lys Ala Pro Leu
        130                 135                 140

Arg Glu Leu Leu Arg Glu Arg Ala Glu Lys Met Gly Gln Asn Leu Asn
145                 150                 155                 160

Arg Ile Pro Tyr Lys Asp Thr Phe Trp Lys Gly Thr Thr Arg Thr Arg
                165                 170                 175

Pro Arg Asn Gly Thr Leu Asn Lys His Ser Gly Ile Asp Phe Lys Gln
                180                 185                 190

Leu Asn Phe Leu Thr Lys Leu Asn Glu Asn His Ser Gly Glu Leu Trp
        195                 200                 205

Lys Gly Arg Trp Gln Gly Asn Asp Ile Val Lys Val Leu Lys Val
        210                 215                 220

Arg Asp Trp Ser Thr Arg Lys Ser Arg Asp Phe Asn Glu Glu Cys Pro
225                 230                 235                 240

Arg Leu Arg Ile Phe Ser His Pro Asn Val Leu Pro Val Leu Gly Ala
                245                 250                 255

Cys Gln Ser Pro Pro Ala Pro His Pro Thr Leu Ile Thr His Trp Met
        260                 265                 270

Pro Tyr Gly Ser Leu Tyr Asn Val Leu His Glu Gly Thr Asn Phe Val
        275                 280                 285

Val Asp Gln Ser Gln Ala Val Lys Phe Ala Leu Asp Met Ala Arg Gly
        290                 295                 300

Met Ala Phe Leu His Thr Leu Glu Pro Leu Ile Pro Arg His Ala Leu
305                 310                 315                 320

Asn Ser Arg Ser Val Met Ile Asp Glu Asp Met Thr Ala Arg Ile Ser
                325                 330                 335

Met Ala Asp Val Lys Phe Ser Phe Gln Cys Pro Gly Arg Met Tyr Ala
                340                 345                 350

Pro Ala Trp Val Ala Pro Glu Ala Leu Gln Lys Lys Pro Glu Asp Thr
        355                 360                 365

Asn Arg Arg Ser Ala Asp Met Trp Ser Phe Ala Val Leu Leu Trp Glu
        370                 375                 380

Leu Val Thr Arg Glu Val Pro Phe Ala Asp Leu Ser Asn Met Glu Ile
385                 390                 395                 400

Gly Met Lys Val Ala Leu Glu Gly Leu Arg Thr Ile Pro Pro Gly Ile
                405                 410                 415

Ser Pro His Val Cys Lys Leu Met Lys Ile Cys Met Asn Glu Asp Pro
                420                 425                 430

Ala Lys Arg Pro Lys Phe Asp Met Ile Val Pro Ile Leu Glu Lys Met
        435                 440                 445

Gln Asp Lys
    450
```